(12) United States Patent
Tang et al.

(10) Patent No.: US 8,901,140 B2
(45) Date of Patent: Dec. 2, 2014

(54) 6-AMINO QUINAZOLINE OR 3-CYANO QUINOLINE DERIVATIVES, PREPARATION METHODS AND PHARMACEUTICAL USES THEREOF

(75) Inventors: Peng Cho Tang, Shanghai (CN); Xin Li, Shanghai (CN); Bin Wang, Shanghai (CN); Jun Wang, Shanghai (CN); Lijun Chen, Shanghai (CN)

(73) Assignees: Jiangsu Hengrui Medicine Co., Ltd., Lianyungang, Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 106 days.

(21) Appl. No.: 13/395,892

(22) PCT Filed: Aug. 26, 2010

(86) PCT No.: PCT/CN2010/001293
§ 371 (c)(1),
(2), (4) Date: Mar. 14, 2012

(87) PCT Pub. No.: WO2011/029265
PCT Pub. Date: Mar. 17, 2011

(65) Prior Publication Data
US 2012/0165352 A1    Jun. 28, 2012

(30) Foreign Application Priority Data

Sep. 14, 2009    (CN) .......................... 2009 1 0195823

(51) Int. Cl.
C07D 401/14    (2006.01)
A61K 31/4709    (2006.01)
C07F 9/6512    (2006.01)
A61P 35/00    (2006.01)

(52) U.S. Cl.
USPC ...................... 514/266.21; 544/284; 544/293

(58) Field of Classification Search
USPC ............... 514/266.1, 266.2, 266.21; 544/283, 544/284, 293
See application file for complete search history.

(56) References Cited

FOREIGN PATENT DOCUMENTS

| CN | 1751033 A | 3/2006 |
|---|---|---|
| CN | 101824029 A | 9/2010 |
| WO | 0018761 A1 | 4/2000 |
| WO | 03089439 A1 | 10/2003 |
| WO | 2005028443 A2 | 3/2005 |
| WO | 2007055514 A1 | 5/2007 |

OTHER PUBLICATIONS

McMahon et al (2001) Pinedo et al (2001).*
Int'l Search Report issued Dec. 9, 2010 in Int'l Application No. PCT/CN2010/001293.
Schlessinger et al, "Growth Factor Signaling by Receptor Tyrosine Kinases," Neuron, vol. 9, pp. 383-391 (1992).
Ma et al, "c-Met: Structure, functions and potential for therapeutic inhibition," Cancer and Metastasis Reviews, vol. 22, pp. 309-325 (2003).
Maulik et al, "Role of the hepatocyte growth factor receptor, c-Met, in oncogenesis and potential for therapeutic inhibition," Cytokine & Growth Factor Reviews, vol. 13, pp. 41-59 (2002).
Tsou et al, "Optimization of 6,7-Disubstituted-4-(arylamino)quinoline-3-carbonitriles as Orally Active, Irreversible Inhibitors of Human Epidermal Growth Factor Receptor-2 Kinase Activity," Journal of Medicinal Chemistry, vol. 48, pp. 1107-1131 (2005).

* cited by examiner

Primary Examiner — Paul V. Ward
(74) Attorney, Agent, or Firm — Panitch Schwarze Belisario & Nadel LLP

(57) ABSTRACT

6-amino quinazoline or 3-cyano quinoline derivatives, preparation methods and pharmaceutical uses thereof are disclosed. Specifically, the present disclosure discloses novel 6-amino quinazoline or 3-cyano quinoline derivatives presented by general formula (I), or tautomers, enantiomers, diastereomers, racemates or pharmaceutically acceptable salts thereof, or metabolites, metabolic precursors or pro-drugs thereof, and their uses as treatment agents especially as protein kinase inhibitors, in which each substitutent group of general formula (I) is as defined in the specification.

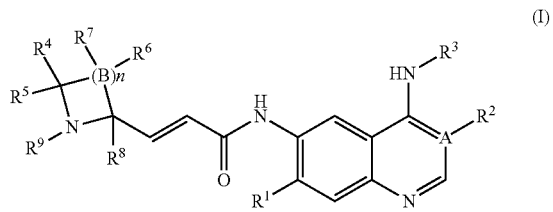

17 Claims, No Drawings

6-AMINO QUINAZOLINE OR 3-CYANO QUINOLINE DERIVATIVES, PREPARATION METHODS AND PHARMACEUTICAL USES THEREOF

CROSS-REFERENCE TO RELATED APPLICATIONS

This application is a Section 371 of International Application No. PCT/CN2010/001293, filed Aug. 26, 2010, which was published in the Chinese language on Mar. 17, 2011, under International Publication No. WO 2011/029265 A1 and the disclosure of which is incorporated herein by reference.

FIELD OF THE INVENTION

The present invention relates to novel 6-amino quinazoline or 3-cyano quinoline derivatives, the preparation methods thereof, pharmaceutical compositions containing such derivatives and the use of such derivatives as therapeutic agents, particularly as protein kinase inhibitors.

BACKGROUND OF THE INVENTION

Signal transduction is a fundamental mechanism whereby extracellular stimuli are relayed to the interior of cells. These signals regulate a wide variety of physical responses in the cell including proliferation, differentiation and apoptosis. Many of these signal transduction processes utilize the reversible phosphorylation process of proteins involving specific protein kinases and phosphatases.

There are two classes of protein kinases (PKs): the protein tyrosine kinases (PTKs) and the serine-threonine kinases (STKs). PTKs can phosphorylate tyrosine residue on a protein. STKs can phosphorylate serine or/and threonine residue. Tyrosine kinases can be divided into either the receptor-type (receptor tyrosine kinase, RTKs) or the non-receptor type (non-receptor tyrosine kinase). Now about 90 tyrosine kinases have been identified in the human genome, of which about 60 belong to the receptor type and about 30 belong to the non-receptor type.

The Receptor Tyrosine Kinases (RTKs) family includes: (1) the EGF family of receptor tyrosine kinases such as the EGFR, HER-2, HER-3 and HER-4; (2) the insulin family of receptor tyrosine kinases such as the insulin receptor (IR) and insulin-like growth factor-I receptor (IGF-IR) and insulin-related receptor (IRR); (3) the Class III family of receptor tyrosine kinases such as the platelet-derived growth factor (PDGF) receptor tyrosine kinases, the stem cell factor receptor tyrosine kinase SCF RTK (commonly known as c-Kit), the fms-related tyrosine kinase 3 (Flt3) receptor tyrosine kinase and the colony-stimulating factor 1 receptor (CSF-1R) tyrosine kinase and the like. Otherwise, hepatocyte growth factor receptor (HGFR)c-Met and vascular endothelial growth factor (VEGFR) belong to RTKs family. They play critical role in the control of cell growth and differentiation and are key mediators of cellular signals leading to the production of cytokines such as growth factors (Schlessinger and Ullrich, *Neuron* 1992, 9, 383).

EGFR(ErbB, HER) play critical role in the control of cell proliferation and growth. These RTKs consist of an extracellular glycosylated ligand binding domain, a transmembrane domain and an intracellular cytoplasm catalytic domain. The enzymatic activity of receptor tyrosine kinases can be stimulated by ligand-mediated homodimerization or heterodimerization. Dimerization results in phosphorylation of tyrosine residues on the receptors in catalytic domain, produces a future binding site. This is followed by the activation of intracellular signaling pathways such as those involving the microtubule associated protein kinase (MAP kinase) and the phosphatidylinositol3-kinase (PI3 kinase). Activation of these pathways has been shown to lead to cell proliferation and the inhibition of apoptosis. It has been identified that such mutated and overexpressed forms of tyrosine kinases, like EGFR, HER-2, are present in a large proportion of common human cancers such as breast cancer, prostate cancer, non-small cell lung cancer, oesophageal cancer, ovarian cancer and pancreatic cancer and the like. Prevalence and relevance of tyrosine kinases is confirmed in the oncogenesis and cancer growth.

As the Class III family of receptor tyrosine kinases, the platelet derived growth factor receptor (PDGFR) group, which includes c-Kit and Fms-like tyrosine kinase 3 (FLT-3), has structure and activation process as same as those of EGFR family. They transmit signals through dimerization, subsequently regulate physical responses in the cell proliferation, differentiation, motility, and vascular growth. Therefore members of this family are closely related with the cancer initiation and development. The expression pattern of c-Kit has been studied e.g. in a panel of different primary solid tumors. A high expression of c-Kit could be found inter alia in small cell bronchial carcinoma, testicular intraepithelial neoplasias, melanomas, mamma carcinomas, neuroblastomas, especially in gastrointestinal stromal tumors (GIST) [see Weber et al., J. Clin. Oncol. 22(14S), 9642 (2004)]. Most (50 to 80%) of GISTS occour through c-Kit gene mutations. Mutations can make c-Kit has continuing activation of receptor tyrosine kinases, leading to a high cell division rate and possibly genomic instability. Thus cancer is induced.

Another important member of receptor tyrosine kinases is the vascular endothelial growth factor receptor (VEGFR). VEGFR is closely involved with angiogenesis. VEGF can activate related signaling pathways to promote angiogenesis by binding with VEGFR. Recent evidence indicates that VEGF can induce endothelial cell proliferation and migration which subsequently leads to the formation of capillary tubes that promote the formation of the hyperpermeable, immature vascular network which nourishs cancer growth. In addition to its angiogenic activity, VEGFR and VEGF may promote tumor growth directly by pro-survival effects in tumor cells. It was observed that VEGFR is highly expressed in a variety of solid malignant tumors, such as lung carcinomas, breast carcinomas, ovarian carcinoma, pancreatic cancer and melanoma. Therefore, the development of tumors can be inhibited by inhibiting VEGFR activation. That is beneficial in the treatment of cancer.

As one member of the RTKs, the hepatocyte growth factor (HGF) receptor (c-Met or HGFR) has been shown in many human cancers to be involved in oncogenesis, tumor invasion and metastasis, as well as enhanced cell motility (see, Ma, P. C. et al. (2003b). Cancer Metastasis Rev, 22, 309-25; Maulik, G. et al. (2002b). Cytokine Growth Factor Rev, 13, 41-59).

As another member of PTKs, Non-receptor Tyrosine Kinases (abbreviated as "NRTKs" or "CTKs") is the protein tyrosine kinases in cytoplasm. Comparing to RTKs, CTKs are lack of an extracellular function domain and a transmembrane domain. The Tyrosine Kinases activation of CTKs is also closely involved with cancer. A more detailed discription of CTKs is provided in Bolen, 1993, Oncogen 8: 2025-2031.

Two main characteristics of cancer are genomic instability and uncontrolled signal pathways for regulating cell cycle and proliferation. Genomic instability leads to changing or losing biological function of key regulting proteins, then interferencing or damaging the signal transduction pathways, and the aberrant signal pathways couldn't regulate and control cell cycle progress and apoptosis normally, while cancer cell can continue to live and proliferate in the state of genetic damage. As the foundation to achieve these regulating progress, PKs including the above discussed RTKs and cytoplasm PTKs (CTKs) are closely involved with oncogenesis and cancer growth, and became the important target for treating cancer.

There is expected to synthetize novel compounds having anti-tumor cell proliferative activities. These compounds are expected to inhibit one or more RTKs, CTKs or STKs, and are useful for treating or ameliorating RTKs, CTKs or STKs mediated, angiogenesis mediated physiological disorders with cell over-proliferation.

Up to now, a series of literatures about protein kinase inhibitors have been disclosed, such as WO00/18761A1, WO2003089439A1, WO2005028443A1, WO2007055514A1. They disclosed quinoline or quinazoline derivatives, the use and the preparation thereof. Hwei-Ru Tsou et al. in *J. Med. Chem.* 48, 1107-1131 (2005), also disclosed quinoline derivatives as protein kinase inhibitors.

Although some protein kinase inhibitors for treating cancers have been disclosed, it still need to develop new compounds which have better curative effect and pharmacokinetic absorption. After continuous efforts, the inventor provides new compounds of formula (I) in the present invention, and discovers that these compounds have shown better efficiency and function.

SUMMARY OF THE INVENTION

In order to overcome the deficiency of the prior art, the present invention is directed to provide 6-amino quinazoline or 3-cyano quinoline derivatives of formula (I), and tautomers, enantiomers, diastereomers, racemates and pharmaceutically acceptable salts thereof, and metabolites, precursor or prodrug thereof,

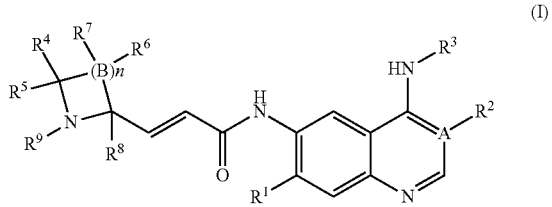

(I)

wherein:
A is selected from the group consisting of carbon atom or nitrogen atom;
when A is carbon atom, $R^1$ is selected from the group consisting of hydrogen or alkoxyl; wherein said alkoxyl is optionally further substituted by one or more groups selected from the group consisting of halogen or alkoxyl; $R^2$ is cyano;
when A is nitrogen atom, $R^1$ is selected from the group consisting of hydrogen or alkoxyl; wherein said alkoxyl is optionally further substituted by one or more groups selected from the group consisting of halogen or alkoxyl; $R^2$ is absent;
$R^3$ is a radical having the following formula:

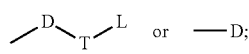

wherein:
D is selected from the group consisting of aryl or heteroaryl, wherein said aryl or heteroaryl is each independently optionally further substituted by one or more groups selected from the group consisting of halogen, alkyl or trifluoromethyl;
T is selected from the group consisting of —(CH$_2$)r-, —O(CH$_2$)r-, —NH(CH$_2$)r- or —S(O)r(CH$_2$)r-;
L is selected from the group consisting of aryl or heteroaryl, wherein said aryl or heteroaryl is each independently optionally further substituted by one or more groups selected from the group consisting of halogen or alkyl;
$R^4$ and $R^5$ are each independently selected from the group consisting of hydrogen, alkyl, alkoxyl, hydroxyl, hydroxyalkyl, halogen, carbonyl, amino, cyano, nitro, carboxy or carboxylic ester;
B is selected from the group consisting of carbon atom, oxygen atom or S(O)r;
when B is carbon atom, $R^6$ and $R^7$ are each independently selected from the group consisting of hydrogen, alkyl, alkoxyl, hydroxyl, hydroxyalkyl, halogen, carbonyl, amino, cyano, nitro, carboxy or carboxylic ester;
when B is oxygen atom or S(O)r, $R^6$ and $R^7$ are absent;
$R^8$ is selected from the group consisting of hydrogen or alkyl;
$R^9$ is selected from the group consisting of hydrogen, alkyl, aryl, carboxy or carboxylic ester;
r is 0, 1, or 2; and
n is 1, 2, 3, 4, or 5.

Preferably, the compounds of formula (I) or tautomers, racemates, enantiomers, diastereomers, and mixtures thereof, and pharmaceutically acceptable salts thereof, wherein A is carbon atom, $R^1$ is alkoxyl; $R^2$ is cyano.

Preferably, the compounds of formula (I) or tautomers, racemates, enantiomers, diastereomers, and mixtures thereof, and pharmaceutically acceptable salts thereof, wherein A is nitrogen atom, $R^1$ is hydrogen; $R^2$ is absent.

Preferably, the compounds of formula (I) or tautomers, racemates, enantiomers, diastereomers, and mixtures thereof, and pharmaceutically acceptable salts thereof, wherein n is 2.

Preferably, the compounds of formula (I) or tautomers, racemates, enantiomers, diastereomers, and mixtures thereof, and pharmaceutically acceptable salts thereof, include the compounds of formula (II) or tautomers, racemates, enantiomers, diastereomers, and mixtures thereof, and pharmaceutically acceptable salts thereof:

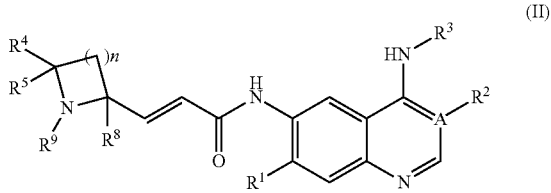

(II)

wherein:
A is selected from the group consisting of carbon atom or nitrogen atom;
when A is carbon atom, $R^1$ is selected from the group consisting of hydrogen or alkoxyl; wherein said alkoxyl is optionally further substituted by one or more groups selected from the group consisting of halogen or alkoxyl; $R^2$ is cyano;
when A is nitrogen atom, $R^1$ is selected from the group consisting of hydrogen or alkoxyl; wherein said alkoxyl is optionally further substituted by one or more groups selected from the group consisting of halogen or alkoxyl; $R^2$ is absent;

$R^3$ is a radical having the following formula:

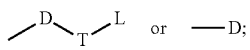

wherein:

D is selected from the group consisting of aryl or heteroaryl, wherein said aryl or heteroaryl is each independently optionally further substituted by one or more groups selected from the group consisting of halogen, alkyl and trifluoromethyl;

T is selected from the group consisting of —(CH$_2$)r-, —O(CH$_2$)r-, —NH(CH$_2$)r- or —S(O)r(CH$_2$)r-;

L is selected from the group consisting of aryl or heteroaryl, wherein said aryl or heteroaryl is each independently optionally further substituted by one or more groups selected from the group consisting of halogen or alkyl;

$R^4$ and $R^5$ are each independently selected from the group consisting of hydrogen, alkyl, alkoxyl, hydroxyl, hydroxyalkyl, halogen, carbonyl, amino, cyano, nitro, carboxy or carboxylic ester;

$R^8$ is selected from the group consisting of hydrogen or alkyl;

$R^9$ is selected from the group consisting of hydrogen, alkyl, aryl, carboxy or carboxylic ester;

r is 0, 1, or 2; and n is 1, 2, 3, 4, or 5.

Preferably, the compounds of formula (II) or tautomers, racemates, enantiomers, diastereomers, and mixtures thereof, and pharmaceutically acceptable salts thereof, wherein A is carbon atom, $R^1$ is alkoxyl; $R^2$ is cyano.

Preferably, the compounds of formula (II) or tautomers, racemates, enantiomers, diastereomers, and mixtures thereof, and pharmaceutically acceptable salts thereof, wherein A is nitrogen atom, $R^1$ is hydrogen; $R^2$ is absent.

Preferably, the compounds of formula (II) or tautomers, racemates, enantiomers, diastereomers, and mixtures thereof, and pharmaceutically acceptable salts thereof, wherein n is 2.

The compounds of the present invention include, but not limited to the following:

| Example No. | Structure and Name |
|---|---|
| 1 | 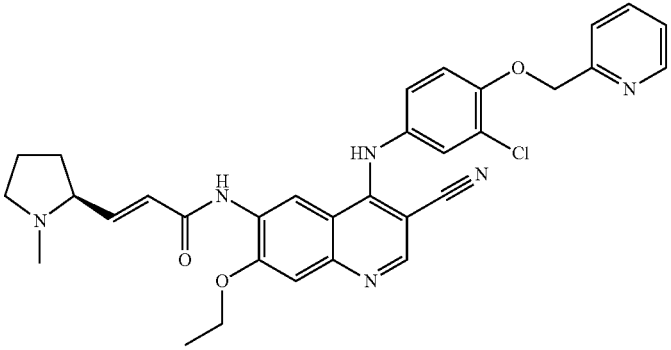 [SMILES: CCOc1cc2ncc(C#N)c(Nc3ccc(OCc4ccccn4)c(Cl)c3)c2cc1NC(=O)/C=C/[C@@H]1CCCN1C]<br>(E)-N-[4-[[3-Chloro-4-(2-pyridylmethoxy)phenyl]amino]-3-cyano-7-ethoxy-6-quinolyl]-3-[(2S)-1-methylpyrrolidin-2-yl]prop-2-enamide |
| 2 | 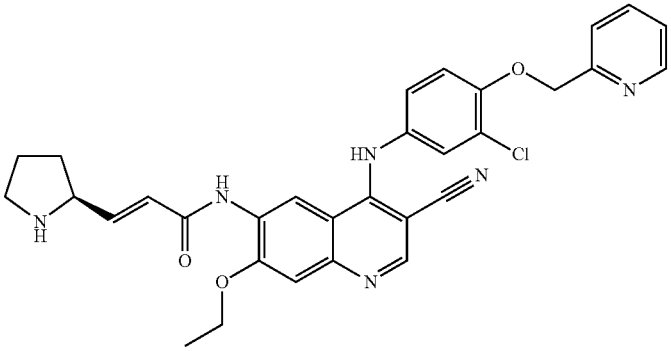 [SMILES: CCOc1cc2ncc(C#N)c(Nc3ccc(OCc4ccccn4)c(Cl)c3)c2cc1NC(=O)/C=C/[C@@H]1CCCN1]<br>(E)-N-[4-[[3-Chloro-4-(2-pyridylmethoxy)phenyl]amino]-3-cyano-7-ethoxy-6-quinolyl]-3-[(2S)-pyrrolidin-2-yl]prop-2-enamide |

-continued
| Example No. | Structure and Name |
|---|---|
| 3 | 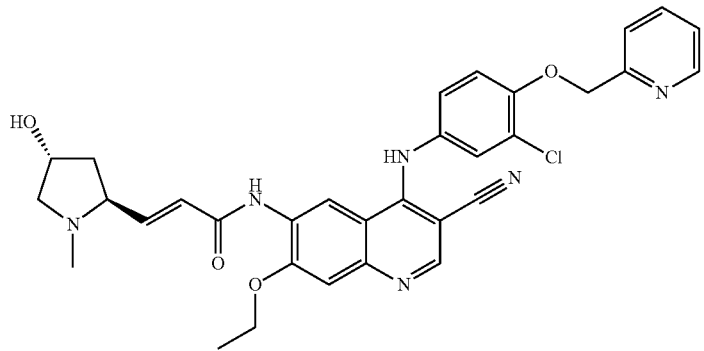 [SMILES: CCOc1cc2ncc(C#N)c(Nc3ccc(OCc4ccccn4)c(Cl)c3)c2cc1NC(=O)/C=C/[C@@H]1C[C@@H](O)CN1C]
(E)-N-[4-[[3-Chloro-4-(2-pyridylmethoxy)phenyl]amino]-3-cyano-7-ethoxy-6-quinolyl]-3-[(2S,4R)-4-hydroxy-1-methyl-pyrrolidin-2-yl]prop-2-enamide |
| 4 | 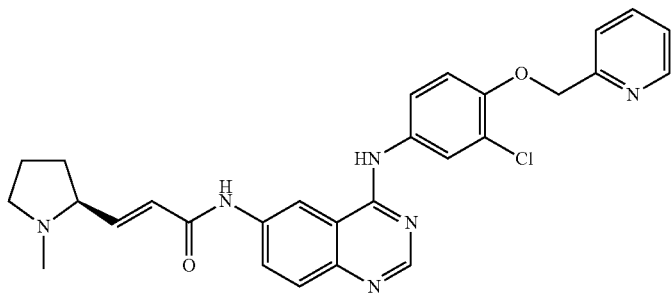 [SMILES: CN1CCC[C@H]1/C=C/C(=O)Nc1ccc2ncnc(Nc3ccc(OCc4ccccn4)c(Cl)c3)c2c1]
(E)-N-[4-[[3-Chloro-4-(2-pyridylmethoxy)phenyl]amino]quinazolin-6-yl]-3-[(2S)-1-methylpyrrolidin-2-yl]prop-2-enamide |
| 5 | 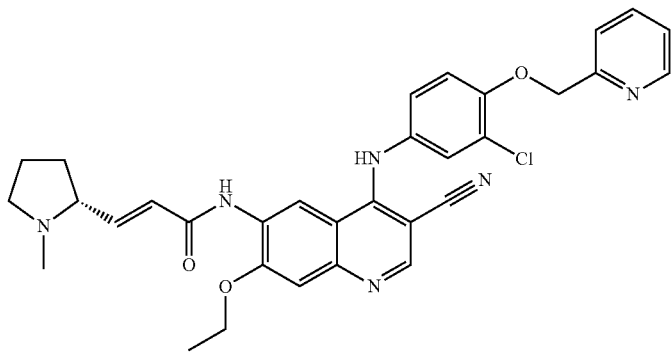
(E)-N-[4-[[3-Chloro-4-(2-pyridylmethoxy)phenyl]amino]-3-cyano-7-ethoxy-6-quinolyl]-3-[(2R)-1-methylpyrrolidin-2-yl]prop-2-enamide |

| Example No. | Structure and Name |
|---|---|
| 6 | 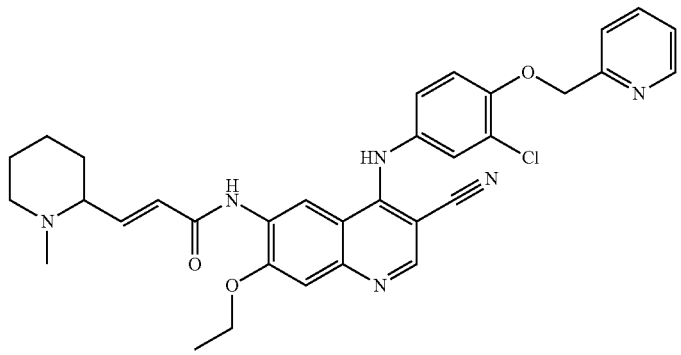 [SMILES: CCOc1cc2ncc(C#N)c(Nc3ccc(OCc4ccccn4)c(Cl)c3)c2cc1NC(=O)/C=C/C1CCCCN1C]<br>(E)-N-[4-[[3-Chloro-4-(2-pyridylmethoxy)phenyl]amino]-3-cyano-7-ethoxy-6-quinolyl]-3-(1-methyl-2-piperidyl)prop-2-enamide |
| 7 | 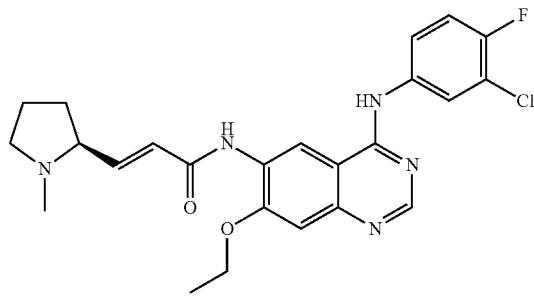 [SMILES: CCOc1cc2ncnc(Nc3ccc(F)c(Cl)c3)c2cc1NC(=O)/C=C/[C@@H]1CCCN1C]<br>(E)-N-[4-[(3-Chloro-4-fluoro-phenyl)amino]-7-ethoxy-quinazolin-6-yl]-3-[(2S)-1-methylpyrrolidin-2-yl]prop-2-enamide |
| 8 | 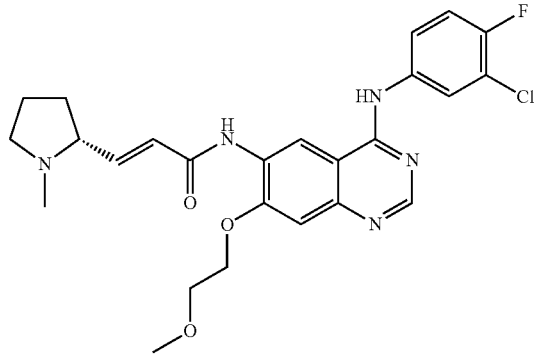 [SMILES: COCCOc1cc2ncnc(Nc3ccc(F)c(Cl)c3)c2cc1NC(=O)/C=C/[C@H]1CCCN1C]<br>(E)-N-[4-[(3-Chloro-4-fluoro-phenyl)amino]-7-(2-methoxyethoxy)quinazolin-6-yl]-3-[(2R)-1-methylpyrrolidin-2-yl]prop-2-enamide |
| 9 | 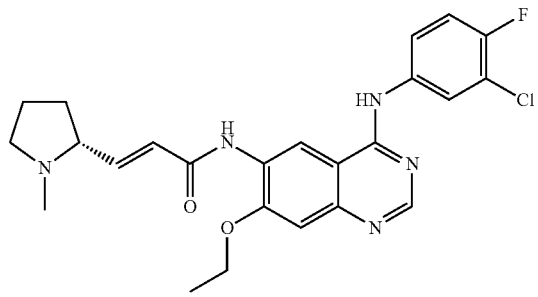 [SMILES: CCOc1cc2ncnc(Nc3ccc(F)c(Cl)c3)c2cc1NC(=O)/C=C/[C@H]1CCCN1C]<br>(E)-N-[4-[(3-Chloro-4-fluoro-phenyl)amino]-7-ethoxy-quinazolin-6-yl]-3-[(2R)-1-methylpyrrolidin-2-yl]prop-2-enamide |

| Example No. | Structure and Name |
|---|---|
| 10 | 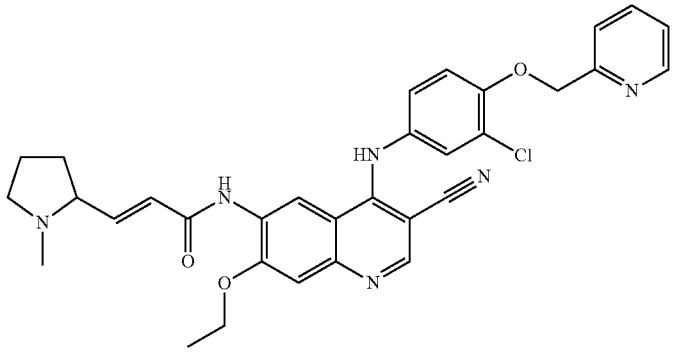 [SMILES: CCOc1cc2ncc(C#N)c(Nc3ccc(OCc4ccccn4)c(Cl)c3)c2cc1NC(=O)/C=C/C1CCCN1C]
(E)-N-[4-[[3-Chloro-4-(2-pyridylmethoxy)phenyl]amino]-3-cyano-7-ethoxy-6-quinolyl]-3-(1-methylpyrrolidin-2-yl)prop-2-enamide | or tautomers, racemates, enantiomers, diastereomers, and mixtures thereof, and pharmaceutically acceptable salts thereof.

In another aspect, this invention relates to compounds having the following formula (IA) as intermediates in the synthesis of compounds of formula (I):

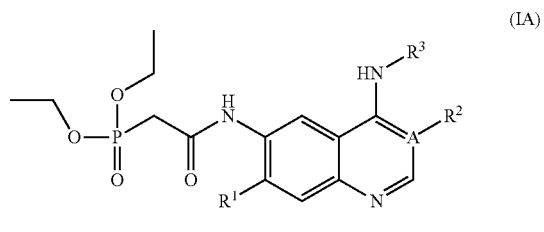

wherein:

A is selected from the group consisting of carbon atom or nitrogen atom;

when A is carbon atom, $R^1$ is selected from the group consisting of hydrogen or alkoxyl; wherein said alkoxyl is optionally further substituted by one or more groups selected from the group consisting of halogen or alkoxyl; $R^2$ is cyano;

when A is nitrogen atom, $R^1$ is selected from the group consisting of hydrogen or alkoxyl; wherein said alkoxyl is optionally further substituted by one or more groups selected from the group consisting of halogen or alkoxyl; $R^2$ is absent;

$R^3$ is a radical having the following formula:

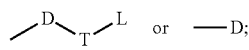

D is selected from the group consisting of aryl or heteroaryl, wherein said aryl or heteroaryl is each independently optionally further substituted by one or more groups selected from the group consisting of halogen, alkyl or trifluoromethyl;

T is selected from the group consisting of —(CH$_2$)r-, —O(CH$_2$)r-, —NH(CH$_2$)r- or —S(O)r(CH$_2$)r-;

L is selected from the group consisting of aryl or heteroaryl, wherein said aryl or heteroaryl is each independently optionally further substituted by one or more groups selected from the group consisting of halogen or alkyl;

r is 0, 1, or 2.

In another aspect, this invention relates to a preparation process of the compound of formula (IA), comprising the following steps of:

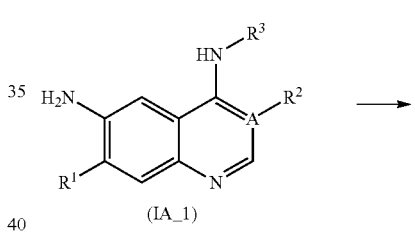

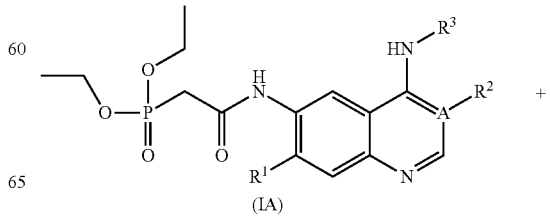

converting the compounds of formula (IA_1) to the compounds of formula (IA); wherein A, $R^1$, $R^2$ and $R^3$ are defined as those in formula (IA).

In another aspect, this invention relates to a preparation process of the compounds of formula (I) or pharmaceutically acceptable salts thereof, comprising the following steps of:

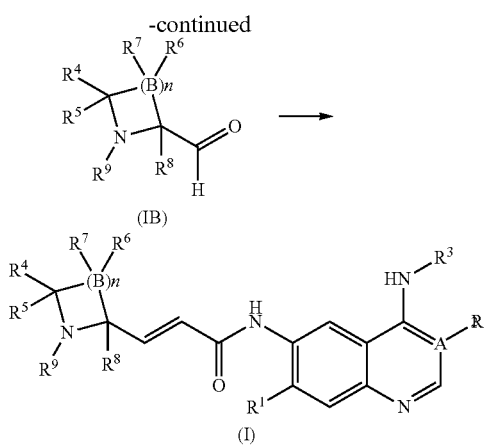

reacting the phosphate compounds of formula (IA) with the compounds of formula (IB) to obtain the compounds of formula (I); wherein A, B, n, $R^1$ to $R^9$ are defined as those in formula (I).

In another aspect, this invention relates to a preparation process of compounds of formula (II) or pharmaceutically acceptable salts thereof, comprising the following steps of:

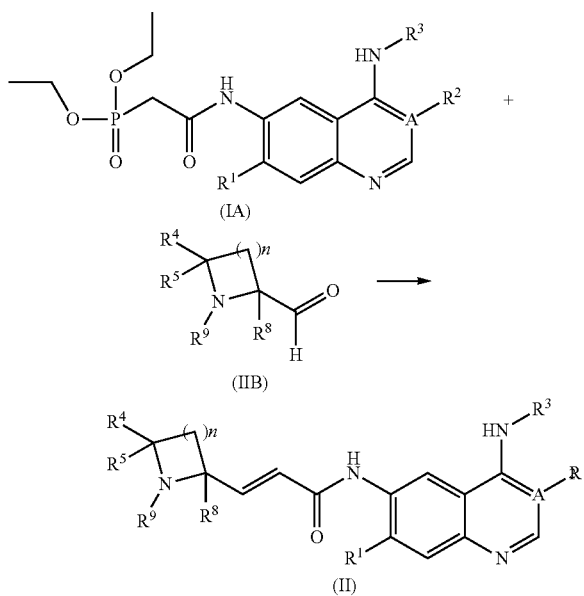

Reacting the compounds of formula (IA) with the compounds of formula (IIB) to obtain the compounds of formula (II); wherein A, n, $R^1$ to $R^5$, $R^8$ and $R^9$ are defined as those in formula (II).

This invention relates to the compounds of formula (I) or tautomers, racemates, enantiomers, diastereomers, and mixtures thereof, and pharmaceutically acceptable salts thereof, for use as receptor tyrosine kinase inhibitors inhibiting VEGFR, EGFR, HER-2, HER-3, HER-4, c-Met, Jak3 or mixtures thereof.

This invention relates to a use of the compounds of formula (I) or tautomers, racemates, enantiomers, diastereomers, and mixtures thereof, and pharmaceutically acceptable salts thereof, in the preparation of receptor tyrosine kinase selected from the group consisting of VEGFR, EGFR, HER-2, HER-3, HER-4, c-Met, Jak3 or mixtures thereof inhibitors.

This invention relates to a use of the compounds of formula (I) or tautomers, racemates, enantiomers, diastereomers, and mixtures thereof, and pharmaceutically acceptable salts thereof, in the preparation of a medicament for the treatment of protein kinases related diseases, wherein said protein kinases are selected from the group consisting of receptor tyrosine kinase, non-receptor tyrosine kinase or serine-threonine kinases; wherein the receptor tyrosine kinase are selected from the group consisting of VEGFR, EGFR, HER-2, HER-3, HER-4, c-Met, Jak3 or mixtures thereof.

In still another aspect, this invention relates to the compounds of formula (I) or tautomers, racemates, enantiomers, diastereomers, and mixtures thereof, and pharmaceutically acceptable salts thereof, for use as a medicament for the treatment of protein kinases related diseases, wherein said protein kinases are selected from the group consisting of receptor tyrosine kinase, non-receptor tyrosine kinase or serine-threonine kinases; wherein the receptor tyrosine kinase are selected from the group consisting of VEGFR, EGFR, HER-2, HER-3, HER-4, c-Met, Jak3 or mixtures thereof.

In still another aspect, this invention relates to a use of the compounds of formula (I) or tautomers, racemates, enantiomers, diastereomers, and mixtures thereof, and pharmaceutically acceptable salts thereof, in the preparation of a medicament for the treatment of cancer, wherein said cancer is selected from the group consisting of lung cancer, breast cancer, squamous cell carcinoma or stomach cancer.

In still another aspect, this invention relates to the compounds of formula (I) or tautomers, racemates, enantiomers, diastereomers, and mixtures thereof, and pharmaceutically acceptable salts thereof, for use as a medicament for the treatment of cancer.

In still another aspect, the present invention relates to a pharmaceutical composition comprising a therapeutically effective amount of the compounds of formula (I), or tautomers, racemates, enantiomers, diastereomers, and mixtures thereof, and pharmaceutically acceptable salts thereof or prodrugs thereof, and pharmaceutically acceptable carriers or excipients. And the present invention also relates to a use of said pharmaceutical composition in the preparation of a medicament for the treatment of protein kinases related diseases, wherein said protein kinases are receptor tyrosine kinases selected from the group consisting of VEGFR, EGFR, HER-2, HER-3, HER-4, c-Met, Jak3 or mixtures thereof. Further the present invention relates to a use of said pharmaceutical composition in the preparation of a medicament for the treatment of cancer, wherein said cancer is selected from the group consisting of lung cancer, breast cancer, squamous cell carcinoma or stomach cancer.

In another aspect, this invention relates to a preparation process of said pharmaceutical composition, comprising the step of combining the compounds of formula (I), or tautomers, racemates, enantiomers, diastereomers, and mixtures thereof, and pharmaceutically acceptable salts thereof or prodrugs thereof with the pharmaceutically acceptable carriers or diluent agents.

In another aspect, the present invention relates to a method of regulating the catalytic activity of protein kinases, comprising contacting the protein kinases with the compounds of formula (I), or tautomers, racemates, enantiomers, diastereomers, and mixtures thereof, and pharmaceutically acceptable salts thereof; wherein the protein kinases are receptor tyrosine kinases selected from the group consisting of VEGFR, EGFR, HER-2, HER-3, HER-4, c-Met, Jak3 or mixtures thereof.

In another aspect, the present invention relates to a method for the treatment of cancer, comprising administrating alone or co-administrating with other drugs to the subject in need thereof a therapeutically effective amount of the compounds of formula (I), or tautomers, racemates, enantiomers, diastereomers, and mixtures thereof, and pharmaceutically acceptable salts thereof, wherein the co-administrated drugs are antitumor drugs selected from the group consisting of Trastuzumab, Herceptin, Cetuximab, Lapatinib, neratinib, Letrozole, Capecitabine, Topotecan, Docetaxel, and so on.

DETAILED DESCRIPTION OF THE INVENTION

Unless otherwise stated, the following terms used in the specification and claims have the meanings discussed below.

"Alkyl" refers to a saturated aliphatic hydrocarbon group including $C_1$-$C_{20}$ straight chain and branched chain groups. Preferably an alkyl group is an alkyl having 1 to 12 carbon atoms. Representative examples include, but are not limited to methyl, ethyl, n-propyl, isopropyl, n-butyl, isobutyl, tert-butyl, sec-butyl, n-pentyl, 1,1-dimethyl propyl, 1,2-dimethyl propyl, 2,2-dimethyl propyl, 1-ethyl propyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and the isomers of branched chain thereof. More preferably an alkyl group is a lower alkyl having 1 to 6 carbon atoms. Representative examples include, but are not limited to methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and etc. The alkyl group may be substituted or unsubstituted. When substituted, the substituent group(s) is preferably one or more groups independently selected from the group consisting of alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocylic alkoxyl, cycloalkylthio, heterocylic alkylthio, carbonyl, carboxy or carboxylic ester.

"Cycloalkyl" refers to saturated and/or partially unsaturated monocyclic or polycyclic hydrocarbon group and have 3 to 20 carbon atoms. Preferably a cycloalkyl group is a cycloalkyl having 3 to 12 carbon atoms. More preferably a cycloalkyl group is a cycloalkyl having 3 to 10 carbon atoms. Representative examples of monocyclic cycloalkyl include, but are not limited to cyclopropyl, cyclobutyl, cyclopentyl, cyclopentenyl, cyclohexyl, cyclohexenyl, cyclohexadienyl, cycloheptyl, cycloheptatrienyl, cyclooctyl and etc. Polycyclic cycloalkyl includes the cycloalkyl having spiro ring, fused ring and bridged ring.

"Spiro Cycloalkyl" refers to 5 to 20 membered polycyclic hydrocarbon group with rings connected through one common carbon atom (called as spiro atom), wherein one or more rings may contain one or more double bonds, but none of the rings has a completely conjugated pi-electron system. Preferably a spiro cycloalkyl is 6 to 14 membered, more preferably is 7 to 10 membered. According to the number of the common spiro atom, spiro cycloalkyl is divided into monocyclic spiro ring, bicyclic spiro ring or multicyclic spiro ring, preferably refers to monocyclic spiro ring or bicyclic spiro ring. More preferably spiro cycloalkyl is 4-membered/4-membered, 4-membered/5-membered, 4-membered/6-membered, 5-membered/5-membered, or 5-membered/6-membered monocyclic spiro ring. Representative examples of spiro cycloalkyl include, but are not limited to the following groups:

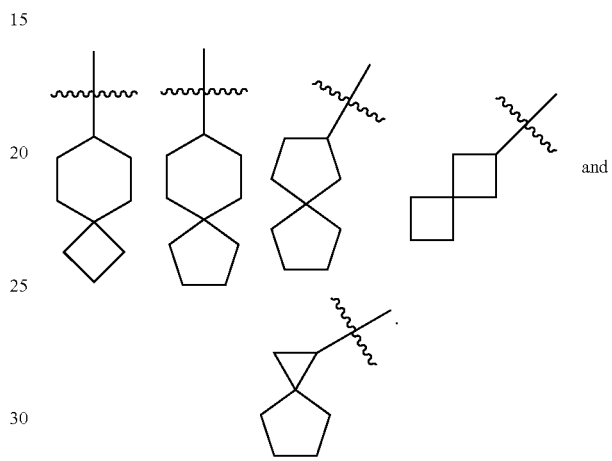

"Fused Cycloalkyl" refers to 5 to 20 membered polycyclic hydrocarbon group, wherein each ring in the system shares an adjacent pair of carbon atoms with other ring, wherein one or more rings may contain one or more double bonds, but none of the rings has a completely conjugated pi-electron system. Preferably a fused cycloalkyl group is 6 to 14 membered, more preferably is 7 to 10 membered. According to the number of membered ring, fused cycloalkyl is divided into fused bicyclic ring, tricyclic ring, tetracyclic ring or multicyclic ring, preferably refers to fused bicyclic ring or tricyclic ring. More preferably fused cycloalkyl is 5-membered/5-membered, or 5-membered/6-membered fused bicyclic ring. Representative examples of fused cycloalkyl include, but are not limited to the following groups:

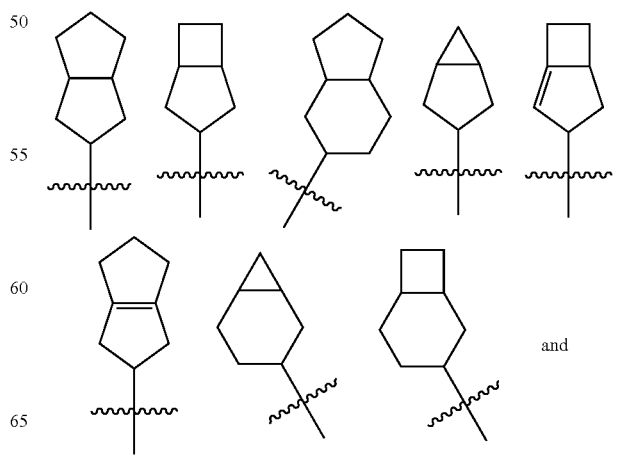

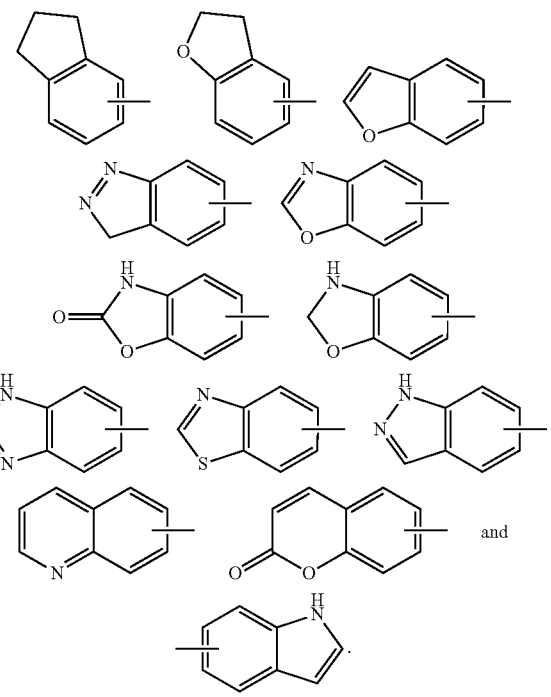

that each ring in the system shares an adjacent pair of carbon atoms with other ring in the system) group, and has a completely conjugated pi-electron system. Preferably aryl is 6 to 10 membered, such as phenyl and naphthyl. The said aryl can be fused to heteroaryl, heterocyclic alkyl or cycloalkyl, wherein the ring connected with parent structure is aryl. Representative examples of aryl include, but are not limited to the following groups:

"Bridged Cycloalkyl" refers to 5 to 20 membered polycyclic hydrocarbon group, wherein every two rings in the system share with two disconnected carbon atoms. The said rings could have one or more double bonds but have no completely conjugated pi-electron system. Preferably a bridged cycloalkyl is 6 to 14 membered, more preferably is 7 to 10 membered. According to the number of membered ring, bridged cycloalkyl is divided into bridged bicyclic ring, tricyclic ring, tetracyclic ring or multicyclic ring, preferably refers to bicyclic ring, tricyclic ring or tetracyclic ring bridged cycloalkyl, more preferably refers to bicyclic ring or tricyclic ring bridged cycloalkyl. Representative examples of bridged cycloalkyl include, but are not limited to the following groups:

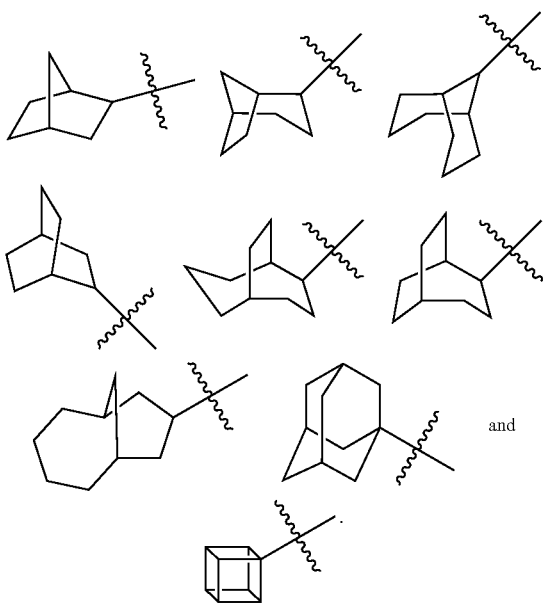

The said cycloalkyl can be fused to aryl, heteroaryl or heterocyclic alkyl, wherein the ring connected with parent structure is cycloalkyl. Representative examples of bridged cycloalkyl include, but are not limited to indanylacetic, tetrahydronaphthalene, 6,7,8,9-tetrahydro-5H-benzo[7]annulene and so on. Said cycloalkyl may be substituted or unsubstituted. When substituted, the substituent group(s) is preferably one or more groups independently selected from the group consisting of alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocylic alkoxyl, cycloalkylthio, heterocylic alkylthio, carbonyl, carboxy or carboxylic ester.

"Aryl" refers to a 6 to 14 membered all-carbon monocyclic ring or a multicyclic fused ring (a "fused" ring system means Said aryl may be substituted or unsubstituted. When substituted, the substituent group(s) is preferably one or more groups independently selected from the group consisting of alkyl, alkenyl, alkynyl, alkyxoyl, alkylsulfo, alkylamino, halogen, thiol, hydroxyl, nitro, cyano, cycloalkyl, heterocyclic alkyl, aryl, heteroaryl, cycloalkoxyl, heterocylic alkoxyl, cycloalkylthio, heterocylic alkylthio, carbonyl, carboxy or carboxylic ester.

"Heteroaryl" refers to an 5-14 membered aryl having 1 to 4 heteroatoms selected from the group consisting of O, S, and N as ring atoms, the remaining ring atoms being C. Preferably, said ring is 6 or 10 membered ring. Preferably, said heteroaryl is 5 or 6 membered ring. Examples of heteroaryl groups are furan, thiophene, pyridine, pyrrole, N-alkyl pyrrole, pyrimidine, pyrazine, imidazole, tetrazolyl, and so on. The said heteroaryl can be fused to aryl, heterocyclic alkyl or cycloalkyl, wherein the ring connected with parent structure is heteroaryl. Representative examples of bridged cycloalkyl include, but are not limited to the following groups:

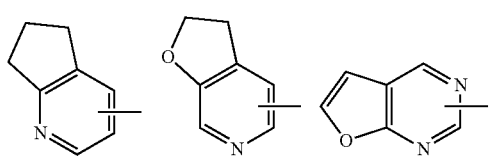

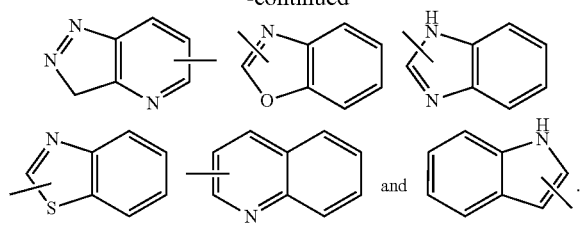 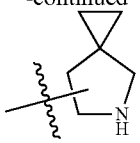

Said heteroaryl may be substituted or unsubstituted. When substituted, the substituent group(s) is preferably one or more groups independently selected from the group consisting of alkyl, alkenyl, alkynyl, alkxoyl, alkylsulfo, alkylamino, halogen, thiol, hydroxyl, nitro, cyano, cycloalkyl, heterocyclic alkyl, aryl, heteroaryl, cycloalkoxyl, heterocylic alkoxyl, cycloalkylthio, heterocylic alkylthio, carbonyl, carboxy or carboxylic ester.

"Heterocyclic alkyl" refers to 3 to 20 membered saturated and/or partially unsaturated monocyclic or polycyclic hydrocarbon group having one or more heteroatoms selected from the group consisting of N, O, or S(O)n (wherein n is 0, 1 or 2) as ring atoms, but excluding —O—O—, —O—S— or —S—S— in the ring, the remaining ring atoms being C. Preferably, heterocyclic alkyl is 3 to 12 membered having 1 to 4 said heteroatoms; more preferably, is 3 to 10 membered. Representative examples of monocyclic heterocyclic alkyl include, but are not limited to pyrrolidyl, piperidyl, piperazinyl, morpholinyl, sulfo-morpholinyl, homopiperazinyl and so on. Polycyclic heterocyclic alkyl includes the heterocyclic alkyl having spiro ring, fused ring and bridged ring.

"Spiro Heterocyclic alkyl" refers to 5 to 20 membered polycyclic heterocyclic alkyl group with rings connected through one common carbon atom (called as spiro atom), wherein said rings have one or more heteroatoms selected from the group consisting of N, O, or S(O)$_p$ (wherein p is 0, 1 or 2) as ring atoms, the remaining ring atoms being C, wherein one or more rings may contain one or more double bonds, but none of the rings has a completely conjugated pi-electron system. Preferably an spiro heterocyclic alkyl is 6 to 14 membered, more preferably is 7 to 10 membered. According to the number of common atom, spiro heterocyclic alkyl is divided into monocyclic spiro heterocyclic alkyl, bicyclic spiro heterocyclic alkyl or multicyclic spiro heterocyclic alkyl, preferably refers to monocyclic spiro heterocyclic alkyl or bicyclic spiro heterocyclic alkyl. More preferably spiro heterocyclic alkyl is 4-membered/4-membered, 4-membered/5-membered, 4-membered/6-membered, 5-membered/5-membered, or 5-membered/6-membered monocyclic spiro heterocyclic alkyl. Representative examples of spiro heterocyclic alkyl include, but are not limited to the following groups:

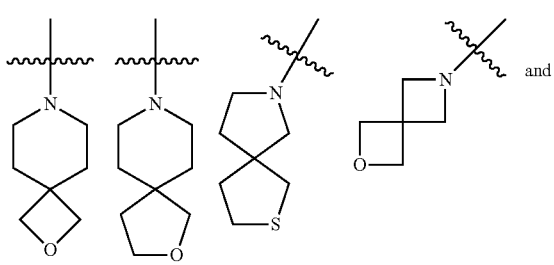

"Fused Heterocyclic alkyl" refers to 5 to 20 membered polycyclic heterocyclic alkyl group, wherein each ring in the system shares an adjacent pair of carbon atoms with other ring, wherein one or more rings may contain one or more double bonds, but none of the rings has a completely conjugated pi-electron system, and wherein said rings have one or more heteroatoms selected from the group consisting of N, O, or S(O)$_p$ (wherein p is 0, 1 or 2) as ring atoms, the remaining ring atoms being C. Preferably an fused Heterocyclic alkyl is 6 to 14 membered, more preferably is 7 to 10 membered. According to the number of membered ring, fused heterocyclic alkyl is divided into fused bicyclic ring, tricyclic ring, tetracyclic ring or multicyclic ring, preferably refers to fused bicyclic ring or tricyclic ring. More preferably fused Heterocyclic alkyl is 5-membered/5-membered, or 5-membered/6-membered fused bicyclic ring. Representative examples of fused heterocyclic alkyl include, but are not limited to the following groups:

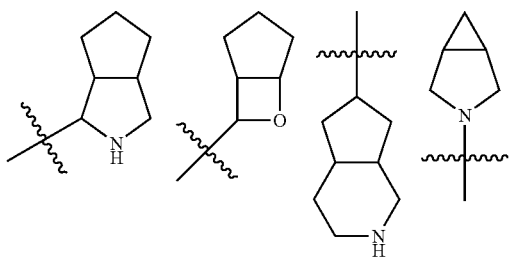

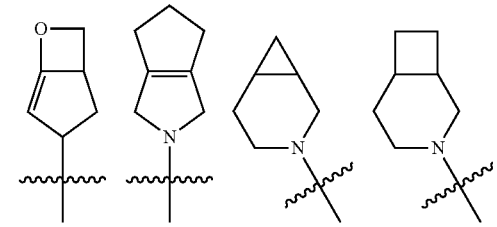

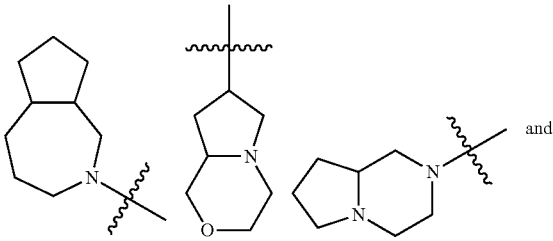

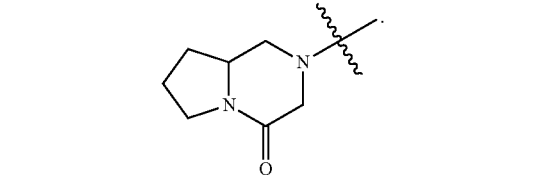

"Bridged Heterocyclic alkyl" refers to 5 to 14 membered polycyclic heterocyclic alkyl group, wherein every two rings in the system share with two disconnected carbon atoms, said rings could have one or more double bonds but have no completely conjugated pi-electron system, said rings have one or more heteroatoms selected from the group consisting of N, O, and S(O)$_p$ (wherein p is 0, 1 or 2) as ring atoms, the remaining ring atoms being C. Preferably an bridged heterocyclic alkyl is 6 to 14 membered, more preferably is 7 to 10 membered. According to the number of membered ring, bridged heterocyclic alkyl is divided into bridged bicyclic ring, tricyclic ring, tetracyclic ring or multicyclic ring, preferably refers to bicyclic ring, tricyclic ring or tetracyclic ring bridged heterocyclic alkyl, more preferably refers to bicyclic ring or tricyclic ring bridged heterocyclic alkyl. Representative examples of bridged heterocyclic alkyl include, but are not limited to the following groups:

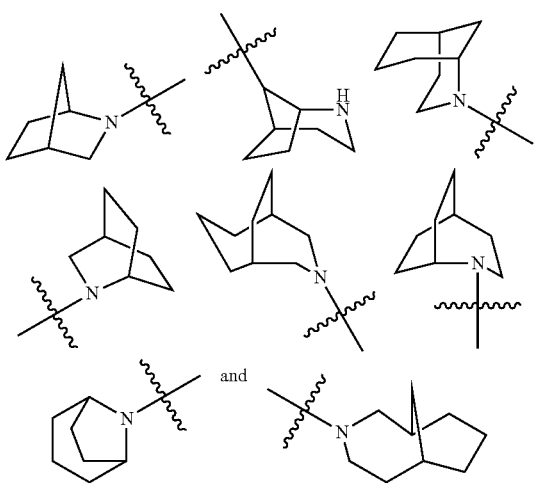

The said heterocyclic alkyl can be fused to aryl, heterocyclic alkyl or cycloalkyl, wherein the ring connected with parent structure is heterocyclic alkyl. Representative examples of heterocyclic alkyl include, but are not limited to the following groups:

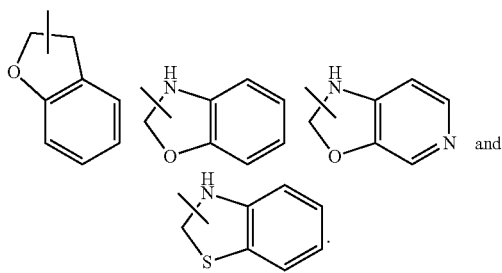

Said heterocyclic alkyl may be substituted or unsubstituted. When substituted, the substituent group(s) is preferably one or more groups independently selected from the group consisting of alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocylic alkoxyl, cycloalkylthio, heterocylic cycloalkylthio, carbonyl, carboxy or carboxylic ester.

"Alkoxyl" refers to both an —O-(alkyl) and an —O-(unsubstituted cycloalkyl) group, wherein alkyl as defined above. Representative examples include, but are not limited to, methoxyl, ethoxyl, propoxyl, butoxyl, cyclopropoxyl, cyclobutoxyl, cyclopentyloxyl, cyclohexyloxyl, and the like. Said alkoxyl may be substituted or unsubstituted. When substituted, the substituent group(s) is preferably one or more groups independently selected from the group consisting of alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocylic alkoxyl, cycloalkylthio, heterocylic cycloalkylthio, carbonyl, carboxy or carboxylic ester.

"Hydroxyl" refers to an —OH group.

"Hydroxyalkyl" refers to -alkyl —OH, wherein alkyl as defined above.

"Halo" refers to fluoro, chloro, bromo, or iodo, preferably fluoro or chloro.

"Carbonyl" refers to —C(=O)—.

"Nitro" refers to —NO$_2$.

"Cyano" refers to —CN.

"Amino" refers to —NH$_2$.

"Carboxy" refers to —C(=O)OH.

"Carboxylic ester" refers to —C(=O)O-alkyl.

"Optional" or "optionally" means that the subsequently described event or circumstance may or may not occur, and that the description includes instances where the event or circumstance may or may not occur. For example, "heterocycle group optionally further substituted by an alkyl group" means that the alkyl may or may not be present, and the description includes situations where the heterocycle group is substituted by an alkyl group and situations where the heterocyclo group is not substituted by the alkyl group.

A "pharmaceutical composition" refers to a mixture of one or more of the compounds described herein, or physiologically/pharmaceutically acceptable salts or prodrugs thereof, with other chemical components, such as physiologically/pharmaceutically acceptable carriers and excipients. The purpose of a pharmaceutical composition is to facilitate administration of a compound to an organism, benefit intaking of active ingredient more effectively.

Synthesis Method of the Invention Compound

In order to complete the purpose of the invention, the invention applies the following technical solution:

A preparation process of the compounds of formula (I) or pharmaceutically acceptable salts thereof according to this invention, comprising the following steps of:

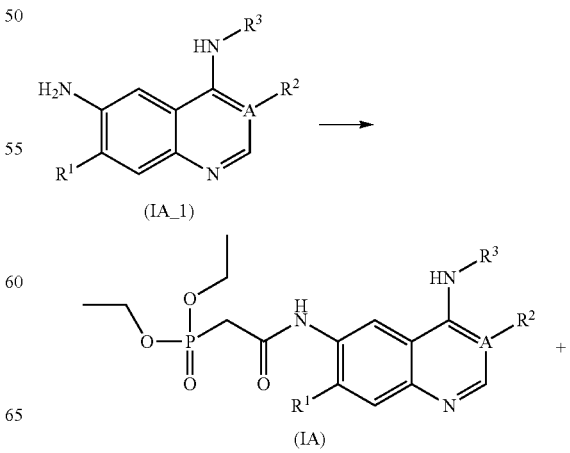

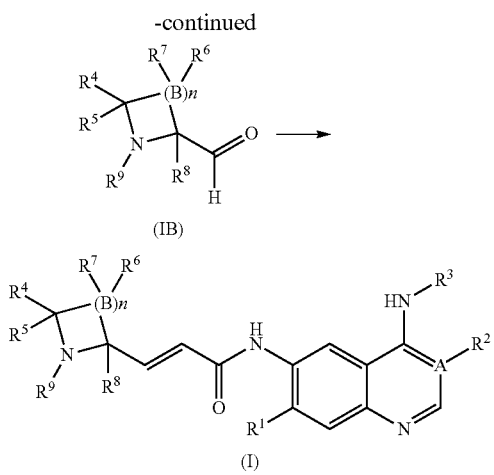

Reacting the compounds of formula (IA-1) with diethylphosphonoacetic acid to obtain the compounds of formula (IA) in the presence of a condensation agent; in a dry ice bath, reacting the compounds of formula (IA) with Lithium bis(trimethylsilyl)amide, heating the reaction solution to room temperature and reacting it with the compounds of formula (IB) via witting reaction to obtain the compounds of formula (I);

Wherein A, B, n and $R^1$ to $R^9$ are as defined in formula (I).

A preparation process of the compounds of formula (II) or pharmaceutically acceptable salts thereof according to this invention, comprising the following steps of:

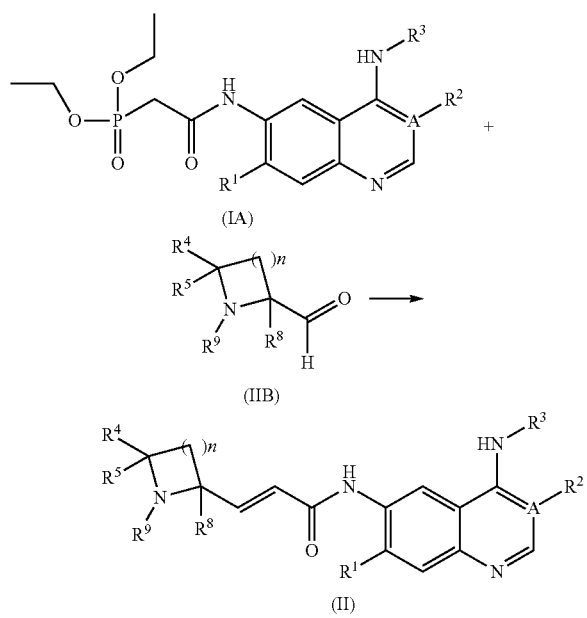

reacting the compounds of the formula (IA) with Lithium bis(trimethylsilyl)amide in a dry ice bath, then heating the reaction solution to room temperature and reacting it with the compounds of formula (IIB) via witting reaction to obtain the compounds of formula (II);

Wherein A, n, $R^1$~$R^5$ and $R^8$~$R^9$ are as defined in formula (II).

Specific Implemention Methods

The present invention is further described by the following Examples which are not intended to limit the scope of the invention.

EXAMPLES

The structures of all compounds were identified by nuclear magnetic resonance ($^1$H NMR) and/or mass spectrometry (MS). $^1$H NMR chemical shifts were recorded as ppm ($10^{-6}$). $^1$H NMR was performed on a Bruker AVANCE-400 spectrometer. The appropriate solvents included deuterated-methanol ($CD_3OD$), deuterated-chloroform ($CDCl_3$) and deuterated-dimethyl sulfoxide (DMSO-$d_6$) with tetramethylsilane (TMS) as the internal standard.

MS was determined on a FINNIGAN LCQ Ad (ESI) mass spectrometer (Thermo, Model: Finnigan LCQ advantage MAX).

HPLC was determined on an Agilent 1200DAD high pressure liquid chromatography spectrometer (Sunfire C18 150× 4.6 mm chromatographic column) and a Waters 2695-2996 high pressure liquid chromatography spectrometer (Gimini C18 150×4.6 mm chromatographic column).

$IC_{50}$ was determined on a NovoStar ELIASA (BMG Co. German).

The thin-layer silica gel used Yantai Huanghai HSGF254 or Qingdao GF254 silica gel plate. The dimension of the plates used in TLC was 0.15 mm to 0.2 mm, and the dimension of the plates used in product purification was 0.4 mm to 0.5 mm.

Column chromatography generally used Yantai Huanghai 200 to 300 mesh silica gel as carrier.

Alkaline alumina column chromatography generally used GuoYao FCP200 to 300 mesh alkaline alumina as carrier.

The starting materials of the present invention are known or purchased from ABCR GmbH & Co. KG, Acros Organics, Aldrich Chemical Company, Accela ChemBio Inc, Darui Finechemical Co., Ltd and so on, or they can be prepared by the conventional synthesis methods in the prior art.

Unless otherwise stated, the following reactions were placed under nitrogen atmosphere or argon atmosphere.

The term "argon atmosphere" or "nitrogen atmosphere" refers to that a reaction flask is equipped with a balloon filled about 1 L nitrogen.

The term "hydrogen atmosphere" refers to that a reaction flask is equipped with a balloon filled about 1 L hydrogen.

Pressured hydrogenation reactions were performed with a Parr 3916EKX hydrogenation spectrometer and a QL-500 hydrogen generator or a HC2-SS hydrogenation spectrometer.

In hydrogenation reactions, the reaction system was generally vacuumed and filled with hydrogen, repeat the above operation three times.

Unless otherwise stated, the solution used in examples refers to an aqueous solution.

Unless otherwise stated, the reaction temperature was room temperature.

Room temperature was the most ambient reaction temperature, which was 20° C.-30° C.

The reactions process of the examples was monitored by thin layer chromatography (TLC). The developing solvent system comprised dichloromethane and methanol system, hexane and ethyl acetate system, petroleum ether and ethyl acetate system, and acetone. The ratio of the volume of the solvent was adjusted according to the polarity of the compounds. The elution system of column chromatography and the developing solvent system of thin layer chromatography comprised: A: dichloromethane and methanol system, B: hexane and ethyl acetate system, C: dichloromethane and acetone system. The ratio of the volume of the solvent was adjusted according to the polarity of the compounds, and sometimes a basic agent such as triethylamine or an acidic agent such as acetic acid was also added.

Example 1

(E)-N-[4-[[3-Chloro-4-(2-pyridylmethoxy)phenyl]amino]-3-cyano-7-ethoxy-6-quinolyl]-3-[(2S)-1-methylpyrrolidin-2-yl]prop-2-enamide

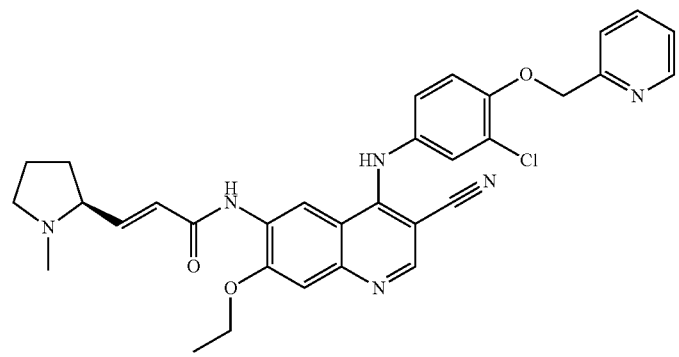

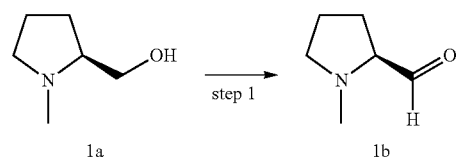

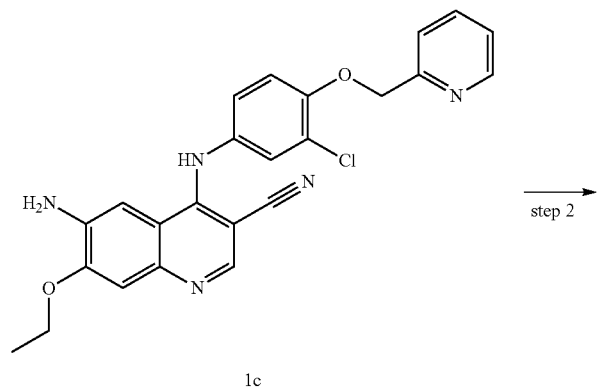

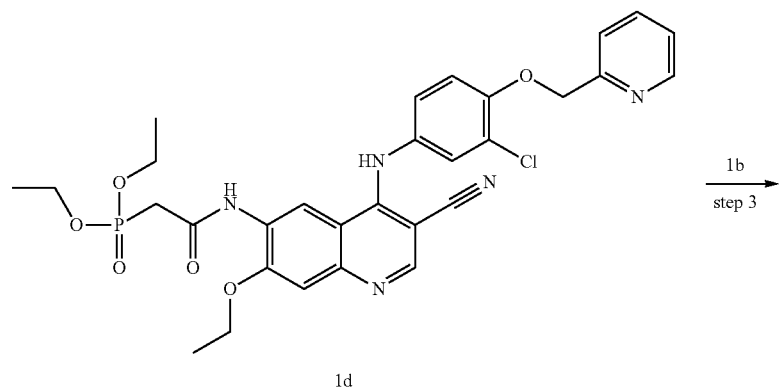

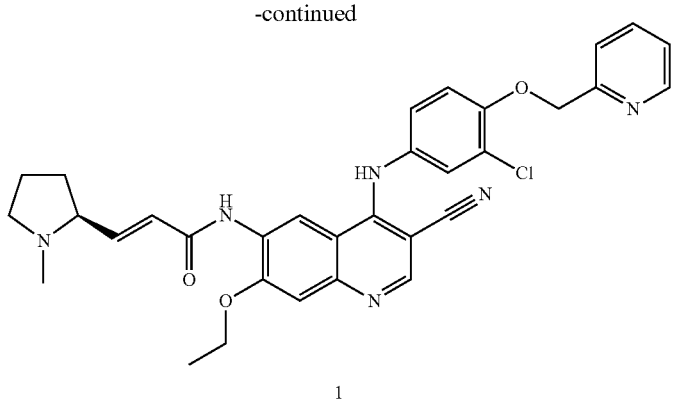

1

Step 1

(2S)-1-Methylpyrrolidine-2-carbaldehyde

Oxalyl chloride (1.1 mL, 13.02 mmol) was dissolved in dimethylsulfoxide (1.9 mL, 26.04 mmol) in a dry ice bath. After 30 minutes, a solution of [(2S)-1-methylpyrrolidin-2-yl]methanol 1a (1 g, 8.68 mmol) in dichloromethane (25 mL) was added dropwise. Then the mixture was stirred at −30° C. for 45 minutes, followed by dropwise addition of triethylamine (6.15 g, 60.77 mmol). The mixture was warmed up to room temperature and stirred for 12 hours. The reaction mixture was added with 250 mL of dichloromethane, washed with saturated sodium bicarbonate (100 mL), saturated ammonium chloride (100 mL) and saturated brine (100 mL) successively. The combined organic extracts were dried over anhydrous sodium sulfate, filtered and concentrated under reduced pressure and the resulting residue was purified by alkaline alumina column chromatography with elution system A to obtain the title compound (2S)-1-methylpyrrolidine-2-carbaldehyde 1b (308 mg, yield 31.4%) as a light yellow oil.

Step 2

N-[4-[[3-Chloro-4-(2-pyridylmethoxy)phenyl] amino]-3-cyano-7-ethoxy-6-quinolyl]-2-diethoxyphosphoryl-acetamide N,N'-Carbonyldiimidazole (487 mg, 3 mmol) was dissolved in 4 mL of tetrahydrofuran. The mixture was heated to 40° C. in an oil bath, a solution of diethylphosphonoacetic acid (588 mg, 3 mmol) in tetrahydrofuran (4 mL) was added dropwise to the mixture, and stirred for 30 minutes to the next step.

6-Amino-4-[[3-chloro-4-(2-pyridylmethoxy)phenyl] amino]-7-ethoxy-quinoline-3-carbonitrile 1c (446 mg, 1 mmol, prepared by the well-known method: patent application WO2005028443) was dissolved in 4 mL of tetrahydrofuran at 40° C., followed by dropwise addition of the above reaction solution. After stirring for 12 hours, the reaction mixture was concentrated under reduced pressure and extracted with dichloromethane (50 mL×3). The combined organic extracts were washed with saturated brine (30 mL×2), dried over anhydrous sodium sulfate, filtered and concentrated under reduced pressure and the resulting residue was purified by silica gel column chromatography with elution system A to obtain the title compound N-[4-[[3-chloro-4-(2-pyridylmethoxy)phenyl]amino]-3-cyano-7-ethoxy-6-quinolyl]-2-diethoxyphosphoryl-acetamide 1d (624 mg, yield 99.9%) as a light yellow solid.

MS m/z (ESI): 624 [M+1]

Step 3

(E)-N-[4-[[3-Chloro-4-(2-pyridylmethoxy)phenyl] amino]-3-cyano-7-ethoxy-6-quinolyl]-3-[(2S)-1-methylpyrrolidin-2-yl]prop-2-enamide N-[4-[[3-Chloro-4-(2-pyridylmethoxy)phenyl]amino]-3-cyano-7-ethoxy-6-quinolyl]-2-diethoxyphosphoryl-acetamide 1d (50 mg, 0.08 mmol) was dissolved in 2 mL of tetrahydrofuran at −78° C., followed by dropwise addition of a solution of lithium bis(trimethylsilyl)amide (1 M) in toluene (80 μL, 0.08 mmol). After the mixture was stirred for 45 minutes, (2S)-1-methylpyrrolidine-2-carbaldehyde 1b (20 mg, 0.17 mmol) was added. After stirring for another 1 hour, the reaction mixture was warmed up to room temperature and stirred for 12 hours. The reaction mixture was added with 1 mL of water and 1 mL of methanol, then the organic extracts were extracted with dichloromethane (50 mL×3). The combined organic extracts were washed with saturated brine (30 mL×2), dried over anhydrous sodium sulfate, filtered and concentrated under reduced pressure and the resulting residue was purified by silica gel column chromatography with elution system A to obtain the title compound (E)-N-[4-[[3-chloro-4-(2-pyridylmethoxy)phenyl]amino]-3-cyano-7-ethoxy-6-quinolyl]-3-[(2S)-1-methylpyrrolidin-2-yl]prop-2-enamide 1 (25 mg, yield 53.5%) as a yellow solid.

MS m/z (ESI): 583 [M+1]

$^1$H NMR (400 MHz, DMSO-d$_6$): δ 9.63 (s, 2H), 8.95 (s, 1H), 8.60 (d, 1H), 8.48 (s, 1H), 7.89 (t, 1H), 7.59 (d, 1H), 7.37 (m, 3H), 7.27-7.20 (m, 2H), 6.80-6.60 (m, 2H), 5.29 (s, 2H), 4.34 (dd, 2H), 2.33-2.24 (m, 3H), 2.23-2.15 (m, 2H), 1.99-1.88 (m, 3H), 1.80-1.78 (m, 2H), 1.49 (t, 3H)

Example 2
(E)-N-[4-[[3-Chloro-4-(2-pyridylmethoxy)phenyl]amino]-3-cyano-7-ethoxy-6-quinolyl]-3-[(2S)-pyrrolidin-2-yl]prop-2-enamide
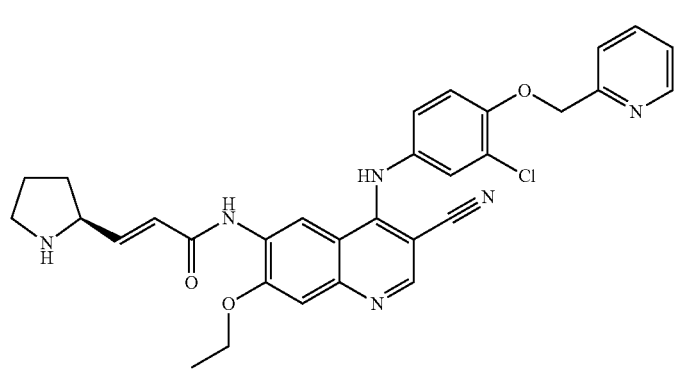
2
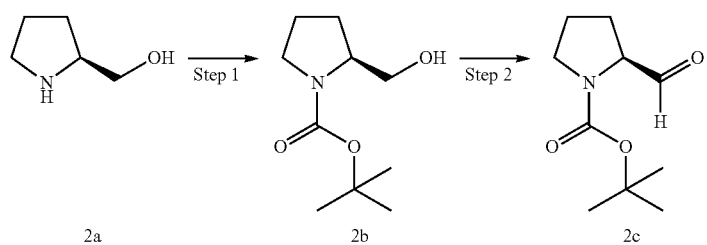
2a  2b  2c
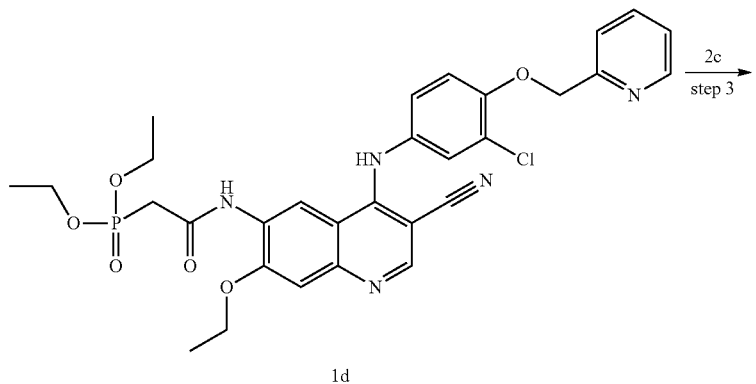
1d
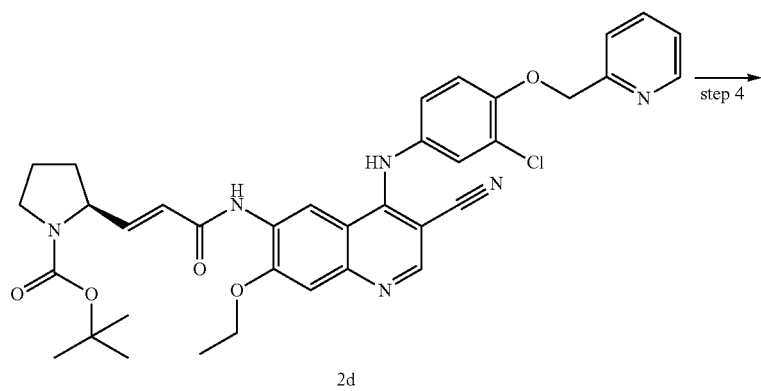
2d

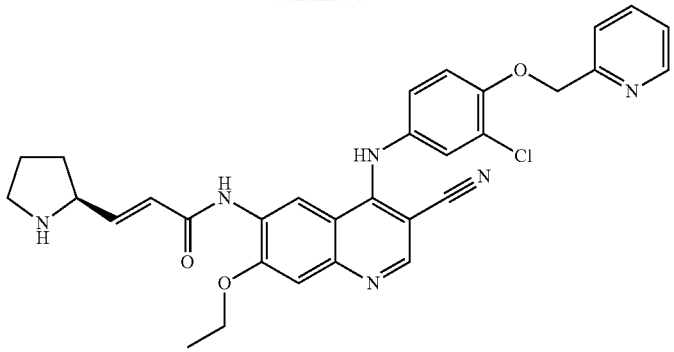

2

Step 1 tert-butyl (2S)-2-(Hydroxymethyl)pyrrolidine-1-carboxylate

[(2S)-Pyrrolidin-2-yl]methanol 2a (5.06 g, 0.05 mmol) and triethylamine (10.12 g, 0.10 mmol) were dissolved in 100 mL of dichloromethane in an ice-water bath. The reaction mixture was added with di-tert-butyl pyrocarbonate (16.37 g, 0.08 mmol) in batches and stirred at room temperature for 12 hours. The reaction mixture was concentrated under reduced pressure, extracted with ethyl acetate (50 mL×3). The combined organic extracts were washed with saturated brine (30 mL×2), dried over anhydrous sodium sulfate, filtered and concentrated under reduced pressure to obtain the title compound tert-butyl (2S)-2-(hydroxymethyl)pyrrolidine-1-carboxylate 2b (10 g, yield 99.9%) as a light yellow oil.

Step 2 tert-Butyl (2S)-2-formylpyrrolidine-1-carboxylate

Oxalyl chloride (3.2 mL, 0.04 mol) and dimethyl sulfoxide (4.3 mL, 0.06 mol) were dissolved in 100 mL of dichloromethane in a dry ice bath. After stirring for 30 minutes, a solution of tert-butyl (2S)-2-(hydroxymethyl)pyrrolidine-1-carboxylate 2b (2 g, 0.01 mol) in 20 mL of dichloromethane was added dropwise. The reaction mixture was stirred for 45 minutes, and triethylamine (7.08 g, 0.07 mol) was added dropwise. After stirring for another 1 hours at 0° C., the reaction mixture was added with 500 mL of dichloromethane. The combined organic layers were washed with saturated brine (100 mL×2), dried over anhydrous sodium sulfate, filtered and concentrated under reduced pressure and the resulting residue was purified by silica gel column chromatography with elution system A to obtain the title compound tert-butyl (2S)-2-formylpyrrolidine-1-carboxylate 2c (1.10 g, yield 55.4%) as a light yellow oil.

Step 3 tert-Butyl (2S)-2-[(E)-3-[[4-[[3-chloro-4-(2-pyridylmethoxy)phenyl]amino]-3-cyano-7-ethoxy-6-quinolyl]amino]-3-oxo-prop-1-enyl]pyrrolidine-1-carboxylate N-[4-[[3-Chloro-4-(2-pyridylmethoxy)phenyl]amino]-3-cyano-7-ethoxy-6-quinolyl]-2-diethoxyphosphoryl-acetamide 1d (156 mg, 0.25 mmol) was dissolved in 3 mL of tetrahydrofuran in a dry ice bath, followed by dropwise addition of a solution of lithium bis(trimethylsilyl)amide (1 M) in toluene (375 µL, 0.38 mmol). After the reaction mixture was stirred for 45 minutes, a solution of tert-butyl (2S)-2-formylpyrrolidine-1-carboxylate 2c (100 mg, 0.50 mmol) in 2 mL of tetrahydrofuran was added. The reaction mixture was stirred for another 1 hour, then warmed up to room temperature and stirred for 12 hours. The reaction mixture was concentrated under reduced pressure and the resulting residue was purified by silica gel column chromatography with elution system A to obtain the title compound tert-butyl (2S)-2-[(E)-3-[[4-[[3-chloro-4-(2-pyridylmethoxy)phenyl]amino]-3-cyano-7-ethoxy-6-quinolyl]amino]-3-oxo-prop-1-enyl]pyrrolidine-1-carboxylate 2d (161 mg, yield 96.2%) as a light yellow solid.

MS m/z (ESI): 669 [M+1]

Step 4

(E)-N-[4-[[3-Chloro-4-(2-pyridylmethoxy)phenyl]amino]-3-cyano-7-ethoxy-6-quinolyl]-3-[(2S)-pyrrolidin-2-yl]prop-2-enamide tert-Butyl (2S)-2-[(E)-3-[[4-[[3-chloro-4-(2-pyridylmethoxy)phenyl]amino]-3-cyano-7-ethoxy-6-quinolyl]amino]-3-oxo-prop-1-enyl]pyrrolidine-1-carboxylate 2d (161 mg, 0.24 mmol) was dissolved in a solution of hydrogen chloride (2M) in 25 mL of 1,4-dioxane. After stirring for 12 hours, the reaction mixture was concentrated under reduced pressure and extracted with dichloromethane (50 mL×3). The combined organic extracts were washed with saturated brine (30 mL×2), dried over anhydrous sodium sulfate, filtered and concentrated under reduced pressure and the resulting residue was purified by silica gel column chromatography with elution system A to obtain the title compound (E)-N-[4-[[3-chloro-4-(2-pyridylmethoxy)phenyl]amino]-3-cyano-7-ethoxy-6-quinolyl]-3-[(2S)-pyrrolidin-2-yl]prop-2-enamide 2 (20 mg, yield 14.6%) as a yellow solid.

MS m/z (ESI): 569.4 [M+1]

$^1$H NMR (400M Hz, DMSO-$d_6$): δ10.01 (s, 1H), 9.76 (s, 1H), 9.71 (s, 2H), 9.40 (s, 1H), 8.92 (s, 1H), 8.61 (s, 1H), 8.60 (s, 1H), 7.90 (t, 1H), 7.60 (d, 1H), 7.58-7.41 (s, 2H), 7.39-7.38 (m, 2H), 6.95 (dd, 1H), 6.79 (d, 1H), 5.29 (s, 1H), 4.35 (t, 2H), 4.21-4.20 (m, 1H), 3.23-3.22 (m, 3H), 2.21-2.20 (m, 1H), 2.039-1.94 (m, 1H), 1.84-1.76 (m, 1H), 1.49 (t, 3H)

Example 3
(E)-N-[4-[[3-Chloro-4-(2-pyridylmethoxy)phenyl]amino]-3-cyano-7-ethoxy-6-quinolyl]-3-[(2S,4R)-4-hydroxy-1-methyl-pyrrolidin-2-yl]prop-2-enamide
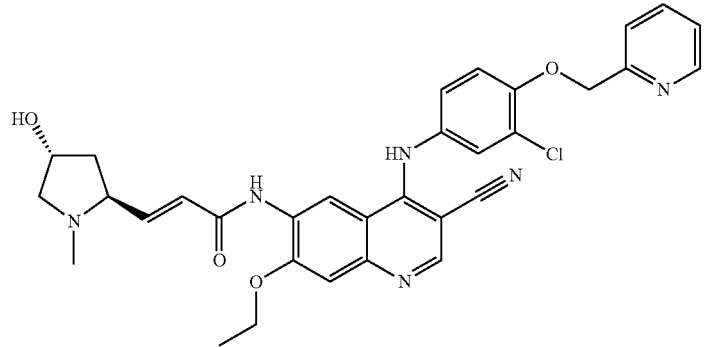
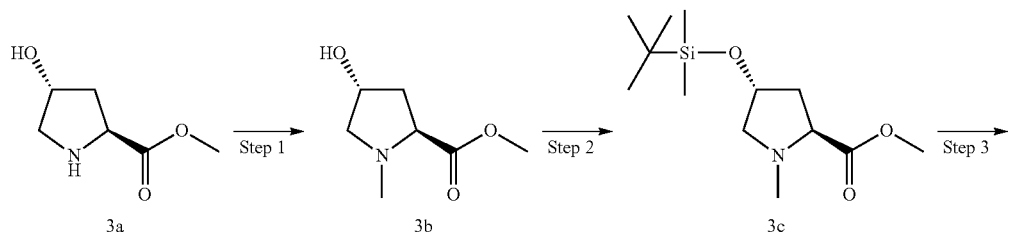
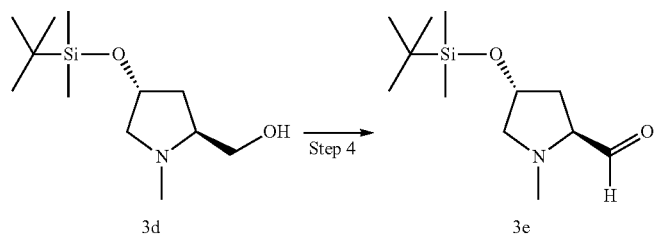
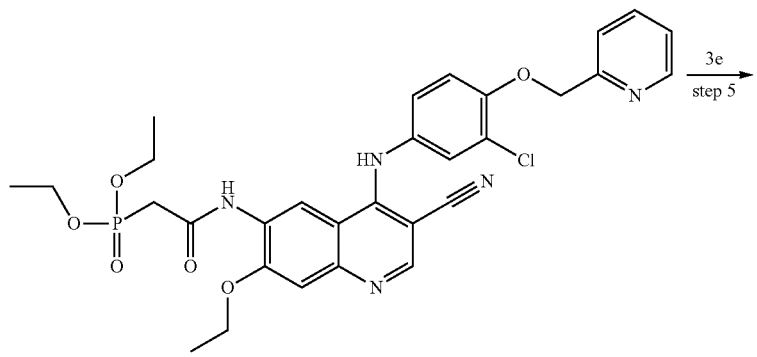

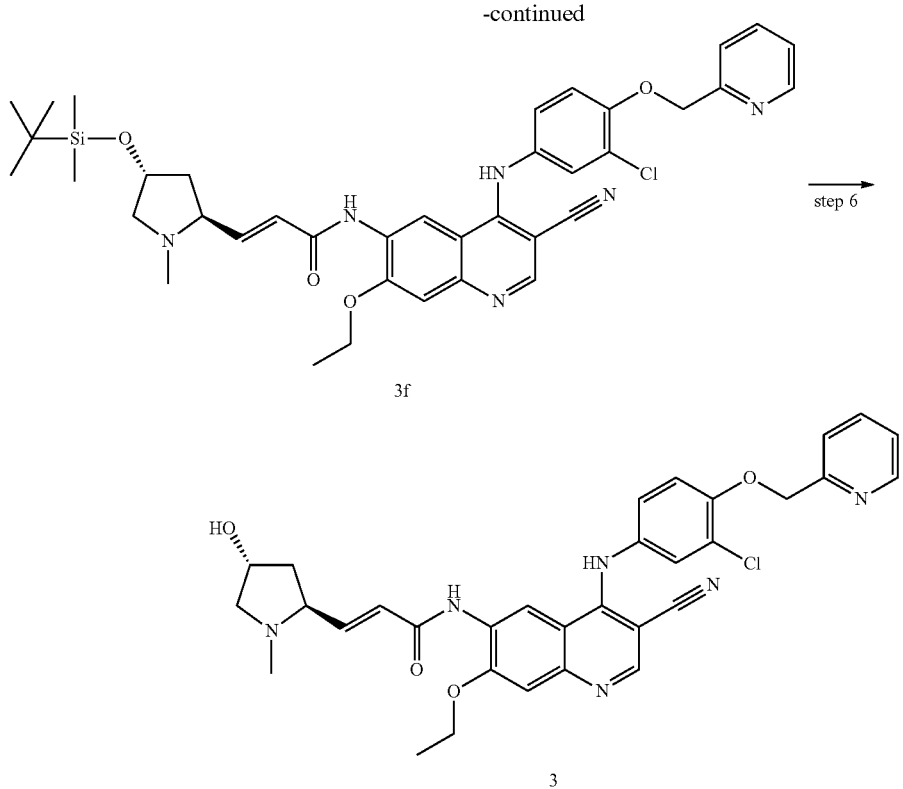

Step 1

Methyl (2S,4R)-4-hydroxy-1-methyl-pyrrolidine-2-carboxylate

Methyl (2S,4R)-4-hydroxypyrrolidine-2-carboxylate 3a (5.53 g, 38 mmol) was dissolved in 80 mL of methanol in an ice-water bath, followed by addition of 40% formaldehyde solution (31 mL, 380 mmol) and sodium cyanoborohydride (12 g, 190 mmol) in batches. The reaction mixture was stirred for 0.5 hours, then warmed up to room temperature and stirred for 3 hours. The mixture was quenched with 40 mL of water, concentrated under reduced pressure and extracted with dichloromethane (80 mL×3). The combined organic extracts were washed with saturated brine (30 mL×2), dried over anhydrous sodium sulfate and filtered. The filtrate was concentrated under reduced pressure to obtain the title compound methyl (2S,4R)-4-hydroxy-1-methyl-pyrrolidine-2-carboxylate 3b crude product as a colourless oil, which was directly used in the next step.

Step 2

Methyl (2S,4R)-4-(tert-butyl(dimethyl)silyl)oxy-1-methyl-pyrrolidine-2-carboxylate Methyl (2S,4R)-4-hydroxy-1-methyl-pyrrolidine-2-carboxylate 3b (6 g, 37 mmol) was dissolved in 100 mL of dichloromethane, followed by addition of imidazole (7.70 g, 113 mmol) and tert-butyl dimethylchlorosilane (6.80 g, 45 mmol) successively. After stirring for 12 hours, the reaction mixture was diluted with 100 mL of dichloromethane, washed with water (50 mL) and saturated brine (50 mL) successively, dried over anhydrous sodium sulfate, filtered and concentrated under reduced pressure and the resulting residue was purified by silica gel column chromatography with elution system A to obtain the title compound methyl (2S,4R)-4-(tert-butyl(dimethyl)silyl)oxy-1-methyl-pyrrolidine-2-carboxylate 3c crude product as a colourless oi, which was directly used in the next step without purification.

MS m/z (ESI): 274 [M+1]

Step 3

[(2S,4R)-4-(tert-Butyl(dimethyl)silyl)oxy-1-methyl-pyrrolidin-2-yl]methanol Methyl(2S,4R)-4-(tert-butyl(dimethyl)silyl)oxy-1-methyl-pyrrolidine-2-carboxylate 3c (2.50 g, 9.10 mmol) was dissolved in 50 mL of dichloromethane in an ice-water bath. Diisobutyl aluminium hydride (18 mL, 18 mmol) was added dropwise slowly, and the mixture was stirred for 6 hours. The reaction mixture was quenched with 1 mL of methanol, diluted with 200 mL of dichloromethane, added with anhydrous sodium sulfate, and stirred for 30 minutes. The reaction mixture was filtered and concentrated under reduced pressure and the resulting residue was purified by alkaline alumina column chromatography with elution system A to obtain the title compound [(2S,4R)-4-(tert-butyl(dimethyesilyl)oxy-1-methyl-pyrrolidin-2-yl]methanol 3d (570 mg, yield 50.0%) as a yellow oil.

MS m/z (ESI): 246 [M+1]

Step 4

(2S,4R)-4-(tert-Butyl(dimethyl)silyl)oxy-1-methyl-pyrrolidine-2-carbaldehyde Dimethyl sulfoxide (174 µL, 2.45 mmol) was dissolved in 20 mL of dichloromethane in a dry ice bath. After the system temperature was stable, oxalyl chloride (156 μL, 1.80 mmol) was added dropwise slowly. After stirring for 30 minutes, a solution of [(2S,4R)-4-(tert-butyl(dimethyl)silyl)oxy-1-methyl-pyrrolidin-2-yl]methanol 3d (300 mg, 1.20 mmol) in 2 mL of dichloromethane was added dropwise. After stirring for 45 minutes, the reaction mixture was added with triethylamine (510 μL, 3.67 mmol), and stirred for 10 minutes, then warmed up to room temperature and stirred for 1 hour. The reaction mixture was diluted with 100 mL of dichloromethane, washed with saturated sodium bicarbonate (20 mL), saturated ammonium chloride (20 mL) and saturated brine (20 mL) successively, dried over anhydrous sodium sulfate, filtered and concentrated under reduced pressure to obtain the title compound (2S,4R)-4-(tert-butyl(dimethyl)silyl)oxy-1-methyl-pyrrolidine-2-carbaldehyde 3e (320 mg) crude product as a yellow oil, which was directly used in the next step.

Step 5

(E)-3-[(2S,4R)-4-(tert-Butyl(dimethyl)silyl)oxy-1-methyl-pyrrolidin-2-yl]-N-[4-[[3-chloro-4-(2-pyridylmethoxy)phenyl]amino]-3-cyano-7-ethoxy-6-quinolyl]prop-2-enamide N-[4-[[3-Chloro-4-(2-pyridylmethoxy)phenyl]amino]-3-cyano-7-ethoxy-6-quinolyl]-2-diethoxyphosphoryl-acetamide 1d (418 mg, 0.67 mmol) was dissolved in 2.5 mL of tetrahydrofuran in a dry ice bath, followed by dropwise addition of a solution of lithium bis(trimethylsilyl)amide (1 M) in toluene (1 mL, 1 mmol). After the mixture was stirred for 45 minutes, a solution of (2S,4R)-4-(tert-butyl(dimethyl)silyl)oxy-1-methyl-pyrrolidine-2-carbaldehyde 3e (326 mg, 1.34 mmol) in 2.5 mL of tetrahydrofuran was added, and stirred for another 1 hour, then warmed up to room temperature and stirred for 12 hours. The reaction mixture was concentrated under reduced pressure and the resulting residue was purified by silica gel column chromatography with elution system A to obtain the title compound (E)-3-[(2S,4R)-4-(tert-butyl(dimethyl)silyl)oxy-1-methyl-pyrrolidin-2-yl]-N-[4-[[3-chloro-4-(2-pyridylmethoxy)phenyl]amino]-3-cyano-7-ethoxy-6-quinolyl]prop-2-enamide 3f (292 mg, yield 61.2%) as a yellow solid.

MS m/z (ESI): 713 [M+1]

Step 6

(E)-N-[4-[[3-Chloro-4-(2-pyridylmethoxy)phenyl]amino]-3-cyano-7-ethoxy-6-quinolyl]-3-[(2S,4R)-4-hydroxy-1-methyl-pyrrolidin-2-yl]prop-2-enamide (E)-3-[(2S,4R)-4-(tert-Butyl(dimethyl)silyl)oxy-1-methyl-pyrrolidin-2-yl]-N-[4-[[3-chloro-4-(2-pyridylmethoxy)phenyl]amino]-3-cyano-7-ethoxy-6-quinolyl]prop-2-enamide 3f (50 mg, 0.07 mmol) and tetrabutyl ammonium fluoride (51 mg, 0.21 mmol) were dissolved in 5 mL of tetrahydrofuran, and the mixture was stirred for 12 hours. The reaction mixture was added with 1 mL of water, concentrated under reduced pressure and extracted with dichloromethane (50 mL×3). The combined organic extracts were washed with saturated brine (30 mL×2), dried over anhydrous sodium sulfate, filtered and concentrated under reduced pressure and the resulting residue was purified by silica gel column chromatography with elution system A to obtain the title compound (E)-N-[4-[[3-chloro-4-(2-pyridylmethoxy)phenyl]amino]-3-cyano-7-ethoxy-6-quinolyl]-3-[(2S,4R)-4-hydroxy-1-methyl-pyrrolidin-2-yl]prop-2-enamide 3 (17 mg, yield 40.4%) as a yellow solid.

MS m/z (ESI): 599.4 [M+1]

$^1$H NMR (400M Hz, DMSO-$d_6$): δ 9.63 (s, 1H), 9.52 (s, 1H), 8.97 (s, 1H), 8.61-8.60 (m, 1H), 8.48 (s, 1H), 7.904-7.862 (m, 1H), 7.60 (d, 1H), 7.41-7.36 (m, 3H), 7.28-7.20 (m, 2H), 6.76 (dd, 1H), 6.61 (d, 1H), 5.29 (s, 2H), 4.82 (s, 1H), 4.35-4.29 (m, 2H), 4.21 (d, 1H), 3.42-3.38 (m, 2H), 3.36-3.33 (m, 3H), 2.93 (d, 1H), 2.41-2.37 (m, 1H), 2.20-2.18 (m, 1H), 1.49 (t, 3H)

Example 4

(E)-N-[4-[[3-Chloro-4-(2-pyridylmethoxy)phenyl]amino]quinazolin-6-yl]-3-[(2S)-1-methylpyrrolidin-2-yl]prop-2-enamide

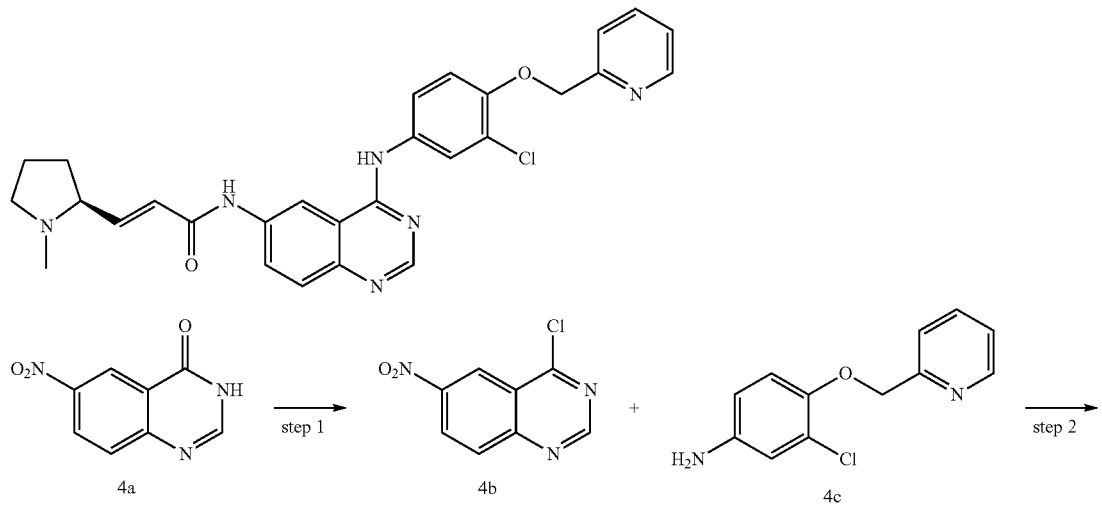

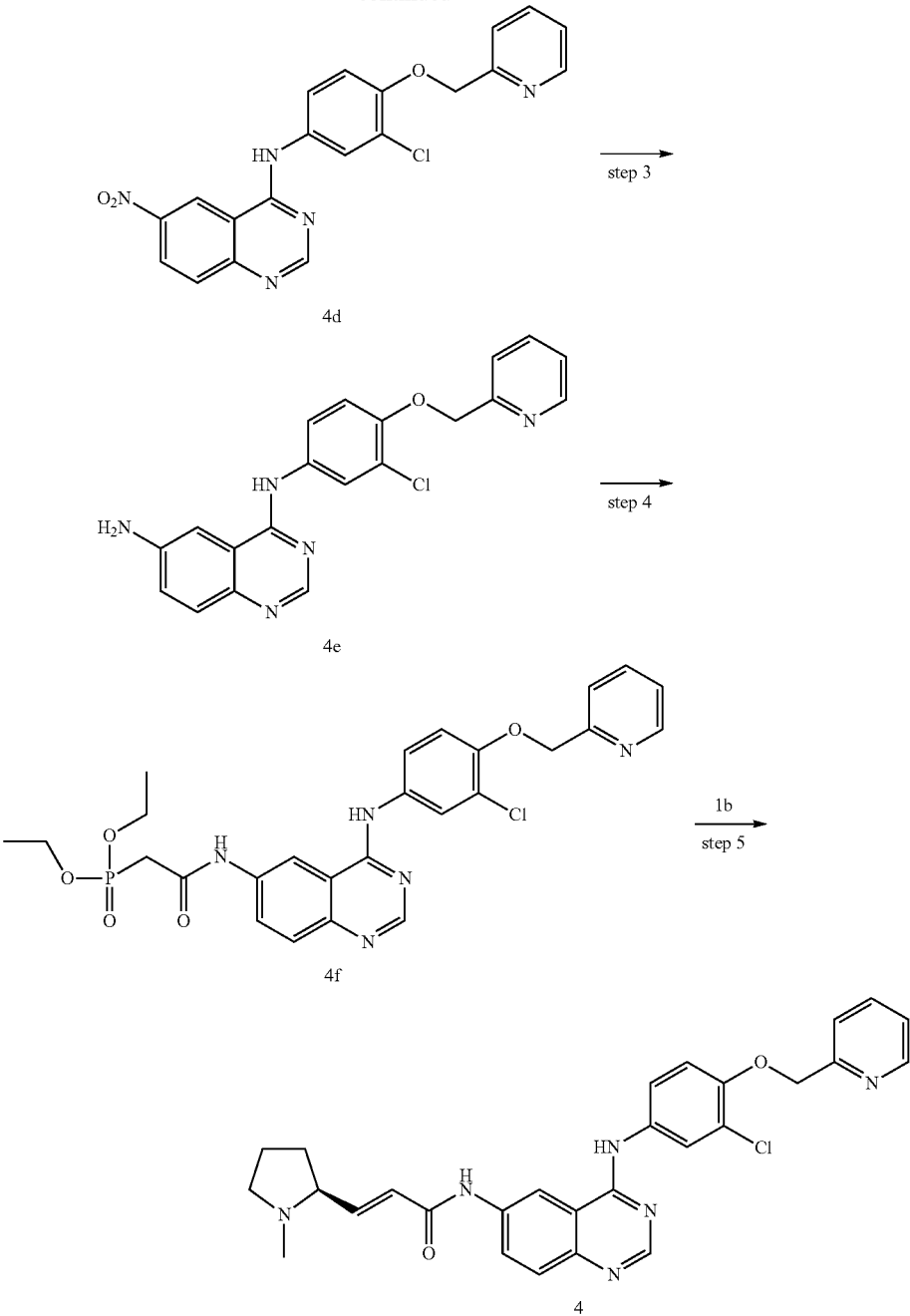

Step 1

4-Chloro-6-nitro-quinazoline

6-Nitro-3H-quinazolin-4-one 4a (18.88 g, 99.40 mmol) was dissolved in phosphoricchloride (31.03 g, 149 mmol). The mixture was warmed up to 160° C., and stirred for 3 hours. The reaction mixture was added to 250 mL of n-hexane while hot, stirred and a lot of the solid was precipitated from the solution, filtered, the filter cake was washed with n-hexane, dried under vacuum to obtain the title compound 4-chloro-6-nitro-quinazoline 4b (18.14 g, yield 87.2%) as a yellow solid.

Step 2

N-[3-Chloro-4-(2-pyridylmethoxy)phenyl]-6-nitro-quinazolin-4-amine

4-Chloro-6-nitro-quinazoline 4b crude product (6.06 g, 28.90 mmol) was dissolved in 100 mL of isopropanol, followed by addition of 3-chloro-4-(2-pyridylmethoxy)aniline 4c (7.47 g, 31.8 mmol). The reaction mixture was heated to reflux for 5 hours. The mixture was cooled to room temperature, the solid was precipitated, filtered and the filter cake was washed with ethyl acetate, saturated brine (50 mL) and water (150 mL) successively, dried under vacuum to obtain the title compound N-[3-chloro-4-(2-pyridylmethoxy)phenyl]-6-nitro-quinazolin-4-amine 4d (8.38 g, yield 74.8%) as a yellow solid.

MS m/z (ESI): 319 [M+1]

Step 3

N4-[3-Chloro-4-(2-pyridylmethoxy)phenyl]quinazoline-4,6-diamine

N-[3-Chloro-4-(2-pyridylmethoxy)phenyl]-6-nitro-quinazolin-4-amine 4d (4.07 g, 10 mmol) and concentrated hydrochloric acid (2 mL, 24 mmol) were dissolved in 130 mL of the solvent mixture of 95% ethanol and water (V/V=10/3), followed by addition of iron powder (11.17 g, 200 mmol). The reaction mixture was heated to reflux for 2 hours, filtered while hot and the filtrate was concentrated under reduced pressure to remove ethanol. The resulting residue was adjusted to pH>7 with ammonium hydroxide, filtered and the filter cake was dried under vacuum, purified by silica gel column chromatography with elution system A to obtain the title compound N4-[3-chloro-4-(2-pyridylmethoxy)phenyl]quinazoline-4,6-diamine 4e (2.04 g, yield 54.1%) as a white solid.

MS m/z (ESI): 378 [M+1]

Step 4

N-[4-[[3-Chloro-4-(2-pyridylmethoxy)phenyl]amino]quinazolin-6-yl]-2-diethoxyphosphoryl-acetamide Diethylphosphonoacetic acid (1.04 g, 5.30 mmol) was dissolved in 10 mL of dichloromethane in an ice-water bath, followed by addition of oxalyl chloride (1.34 g, 10 mmol) and 1 drop of N,N-dimethylformamide. After stirring for 1 hour, the mixture was warmed up to room temperature and stirred for another 1 hour, concentrated under reduced pressure, and added with 10 mL of tetrahydrofuran to the next step.

N4-[3-chloro-4-(2-pyridylmethoxy)phenyl]quinazoline-4,6-diamine 4e (1 g, 2.65 mmol) was dissolved in N,N-diisopropylethylamine (1.03 g, 7.94 mmol), followed by dropwise addition of the above reaction solution. The mixture was warmed up to room temperature and stirred for 1 hour. The reaction mixture was concentrated under reduced pressure and extracted with dichloromethane (50 mL×3). The combined organic extracts were washed with saturated brine (30 mL×2), dried over anhydrous sodium sulfate, filtered and concentrated under reduced pressure and the resulting residue was purified by silica gel column chromatography with elution system A to obtain the title compound N-[4-[[3-chloro-4-(2-pyridylmethoxy)phenyl]amino]quinazolin-6-yl]-2-diethoxyphosphoryl-acetamide 4f (671 mg, yield 45.7%) as a brown solid.

MS m/z (ESI): 556 [M+1]

Step 5

(E)-N-[4-[[3-Chloro-4-(2-pyridylmethoxy)phenyl]amino]quinazolin-6-yl]-3-[(2S)-1-methylpyrrolidin-2-yl]prop-2-enamide N-[4-[[3-Chloro-4-(2-pyridylmethoxy)phenyl]amino]quinazolin-6-yl]-2-diethoxyphosphoryl-acetamide 4f (277 mg, 0.50 mmol) was dissolved in 2.5 mL of tetrahydrofuran in a dry ice bath, followed by dropwise addition of a solution of lithium bis(trimethylsilyl)amide (1 M) in toluene (750 μL, 0.75 mmol). After stirring for 45 minutes, the reaction mixture was added with (2S)-1-methylpyrrolidine-2-carbaldehyde 1b (113 mg, 2 mmol), and stirred for 1 hour, then warmed up to room temperature and stirred for 12 hours. The reaction mixture was concentrated under reduced pressure and the resulting residue was purified by silica gel column chromatography with elution system A to obtain the title compound (E)-N-[4-[[3-chloro-4-(2-pyridylmethoxy)phenyl]amino]quinazolin-6-yl]-3-[(2S)-1-methylpyrrolidin-2-yl]prop-2-enamide 4 (85 mg, yield 33.0%) as a yellow solid.

MS m/z (ESI): 515.3 [M+1]

$^1$H NMR (400 MHz, DMSO-d$_6$): δ 10.47 (s, 1H), 9.82 (s, 1H), 8.79 (s, 1H), 8.61 (d, 1H), 8.52 (s, 1H), 8.00 (s, 1H), 7.91-7.89 (m, 2H), 7.78-7.69 (m, 2H), 7.61 (d, 1H), 7.38 (d, 1H), 7.28 (d, 1H), 6.78-6.72 (m, 1H), 6.47 (d, 1H), 5.30 (s, 2H), 3.14-3.00 (m, 2H), 3.001 (s, 1H), 2.31 (m, 4H), 2.10-2.07 (m, 1H), 1.81 (m, 2H), 1.63 (m, 1H)

Example 5

(E)-N-[4-[[3-Chloro-4-(2-pyridylmethoxy)phenyl]amino]-3-cyano-7-ethoxy-6-quinolyl]-3-[(2R)-1-methylpyrrolidin-2-yl]prop-2-enamide

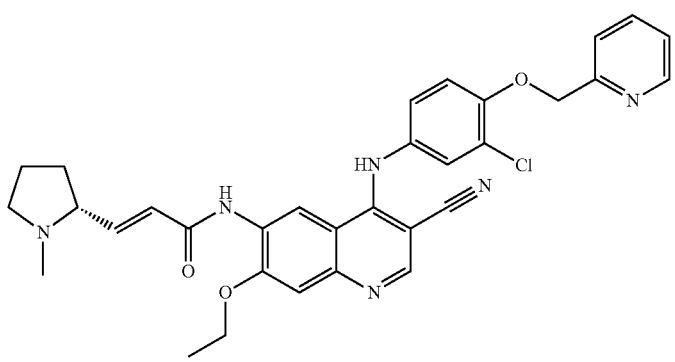

5

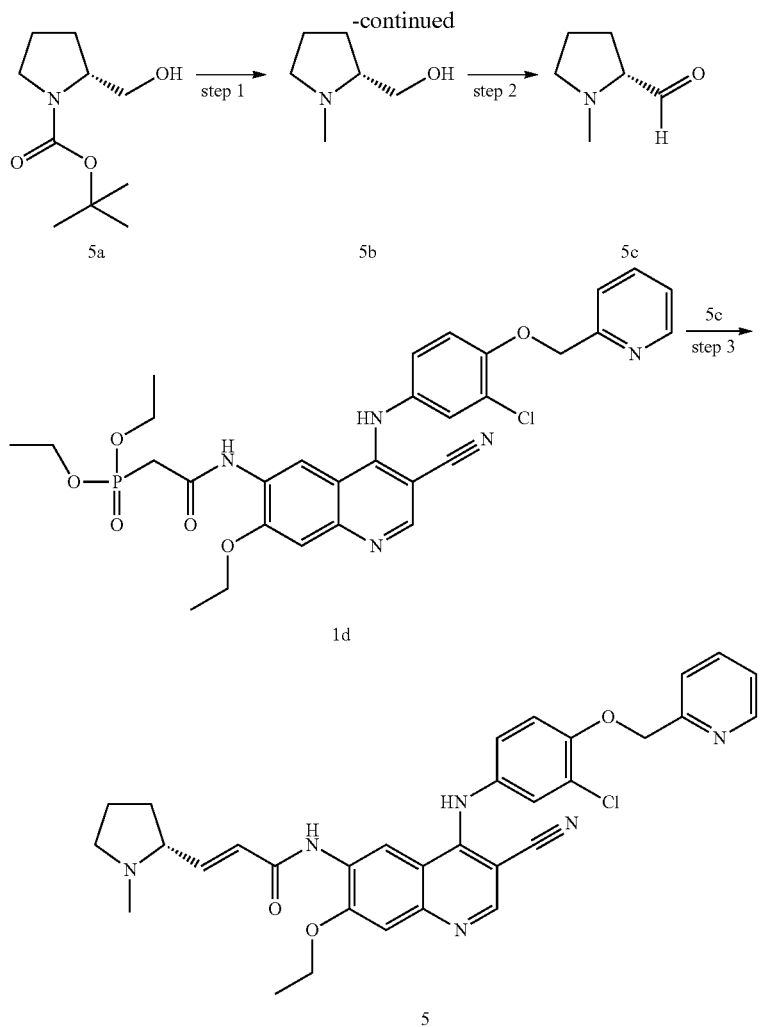

Step 1

[(2R)-1-Methylpyrrolidin-2-yl]methanol

Lithium aluminium hydride (230 mg, 6 mmol) and N-tert-butoxycarbonyl-L-prolinol 5a (400 mg, 2 mmol) were dissolved in 10 mL of dry tetrahydrofuran in an ice-water bath in batches. After no gas was released obviously, the reaction mixture was heated to reflux for 2 hours. The reaction mixture was added dropwise with 5 mL of methanol in an ice-water bath, followed by addition of 5 mL of water, dried over anhydrous magnesium sulfate, filtered and concentrated under reduced pressure to obtain the title compound [(2R)-1-methylpyrrolidin-2-yl]methanol 5b (221 mg, yield 77.0%) as a colourless oil.

MS m/z (ESI): 116 [M+1]

Step 2

(2R)-1-Methylpyrrolidine-2-carbaldehyde

Dimethyl sulfoxide (820 μL, 11.46 mmol) was dissolved in 5 mL of dichloromethane in a dry ice bath, followed by dropwise slowly addition of oxalyl chloride (968 mg, 7.64 mmol). After stirring for 45 minutes, a solution of [(2R)-1-methylpyrrolidin-2-yl]methanol 5b (220 mg, 1.91 mmol) in 2 mL of dichloromethane was added to the solution. The reaction mixture was stirred for 45 minutes, and triethylamine (1.9 mL, 13.37 mmol) were added. The reaction mixture was stirred for 10 minutes, then warmed up to room temperature and stirred for 1 hour. The reaction mixture was washed with water (20 mL) and saturated brine (10 mL) successively. The combined organic extracts were dried over anhydrous sodium sulfate, filtered and concentrated under reduced pressure and the resulting residue was purified by alkaline alumina column chromatography with elution system A to obtain the title compound (2R)-1-methylpyrrolidine-2-carbaldehyde 5c (300 mg) as a yellow solid, which was directly used in the next step without purification.

Step 3

(E)-N-[4-[[3-Chloro-4-(2-pyridylmethoxy)phenyl]amino]-3-cyano-7-ethoxy-6-quinolyl]-3-[(2R)-1-methylpyrrolidin-2-yl]prop-2-enamide N-[4-[[3-Chloro-4-(2-pyridylmethoxy)phenyl]amino]-3-cyano-7-ethoxy-6-quinolyl]-2-diethoxyphosphoryl-acetamide 1d (250 mg, 0.40 mmol) was dissolved in 10 mL of dry tetrahydrofuran in a dry ice bath, followed by dropwise addition of a solution of lithium bis(trimethylsilyl)amide (1 M) in toluene (440 μL, 0.44 mmol). The reaction mixture was stirred for 30 minutes, added dropwise with a solution of (2R)-1-methylpyrrolidine-2-carbaldehyde 5c (90 mg, 0.80 mmol) in 5 mL of tetrahydrofuran, and stirred for 30 minutes, then warmed up to room temperature and stirred for 12 hours. The reaction mixture was concentrated under reduced pressure and the resulting residue was purified by silica gel column chromatography with elution system A to obtain the title compound (E)-N-[4-[[3-chloro-4-(2-pyridylmethoxy)phenyl]amino]-3-cyano-7-ethoxy-6-quinolyl]-3-[(2R)-1-methylpyrrolidin-2-yl]prop-2-enamide 5 (46 mg, yield 19.7%) as a yellow solid.

MS m/z (ESI): 583.4 [M+1]

$^1$H NMR (400 MHz, DMSO-d$_6$): δ 9.16 (s, 1H), 8.63 (d, 1H), 8.56 (s, 1H), 8.26 (s, 1H), 7.83-7.80 (dd, 1H), 7.76-7.50 (m, 2H), 7.57-7.56 (m, 1H), 7.40 (s, 1H), 7.38 (s, 1H), 7.19 (d, 1H), 7.06-7.03 (m, 2H), 6.34-6.31 (d, 1H), 5.35 (s, 2H), 4.39 (m, 2H), 4.27-4.26 (m, 1H), 3.32 (m, 1H), 3.10 (m, 1H), 2.73 (s, 3H), 2.37-2.36 (m, 2H), 2.07-2.01 (m, 2H), 1.64 (t, 3H)

Example 6

(E)-N-[4-[[3-Chloro-4-(2-pyridylmethoxy)phenyl]amino]-3-cyano-7-ethoxy-6-quinolyl]-3-(1-methyl-2-piperidyl)prop-2-enamide

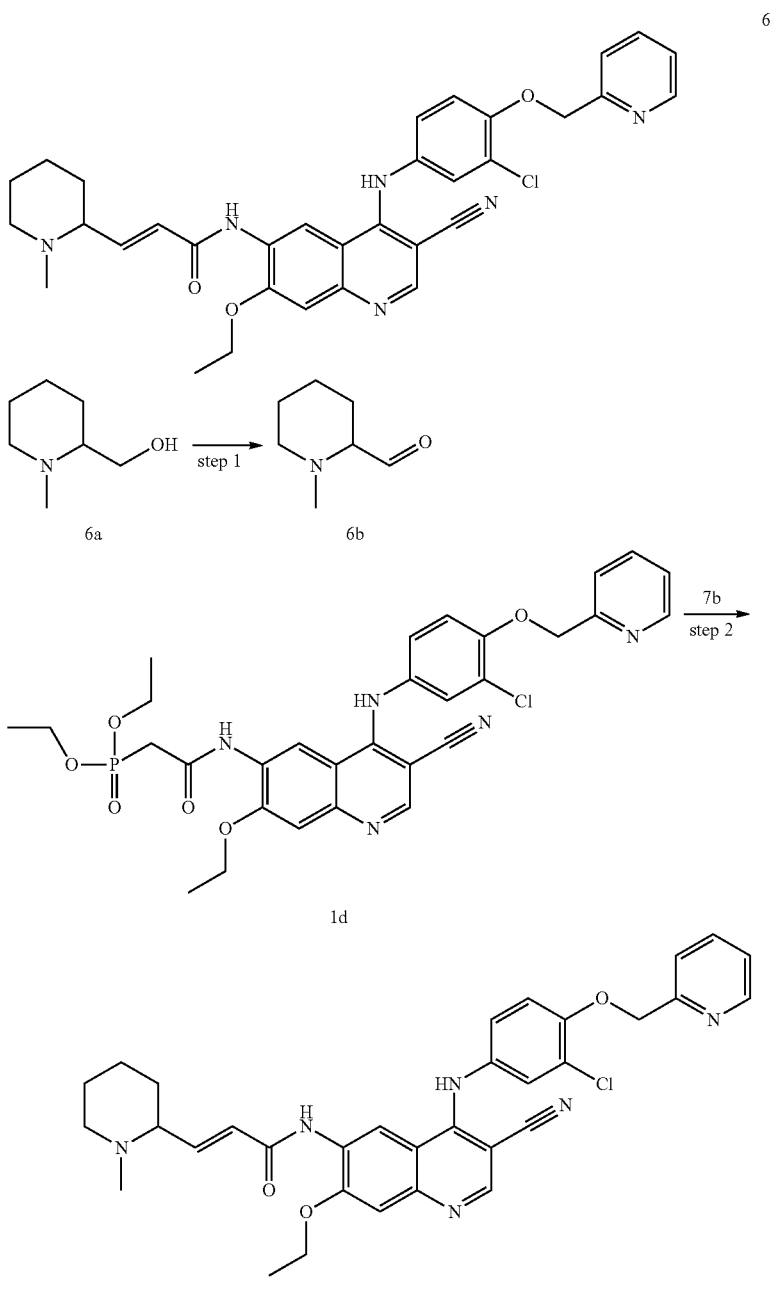

Step 1

1-Methylpiperidine-2-carbaldehyde

Dimethyl sulfoxide (3.3 mL, 46 mmol) was dissolved in 15 mL of dichloromethane in a dry ice bath, followed by dropwise slowly addition of oxalyl chloride (2.6 mL, 31 mmol). After stirring for 45 minutes, a solution of (1-methyl-2-piperidyl)methanol 6a (1 g, 7.74 mmol) in 5 mL of dichloromethane was added dropwise to the solution. The reaction mixture was stirred for 45 minutes, then added with triethylamine (7.2 mL, 52 mmol), and stirred for 10 minutes, then warmed up to room temperature and stirred for 1 hour. The reaction mixture was washed with water (20 mL) and saturated brine (20 mL) successively. The combined organic extracts were dried over anhydrous sodium sulfate, filtered and concentrated under reduced pressure then the resulting residue was purified by alkaline alumina column chromatography with elution system A to obtain the title compound 1-methylpiperidine-2-carbaldehyde 6b (300 mg, yield 31.0%) as a brown oil, which was directly used in the next step without purification.

Step 2

(E)-N-[4-[[3-Chloro-4-(2-pyridylmethoxy)phenyl]amino]-3-cyano-7-ethoxy-6-quinolyl]-3-(1-methyl-2-piperidyl)prop-2-enamide N-[4-[[3-Chloro-4-(2-pyridylmethoxy)phenyl]amino]-3-cyano-7-ethoxy-6-quinolyl]-2-diethoxyphosphoryl-acetamide 1d (300 mg, 0.48 mmol) was dissolved in 10 mL of tetrahydrofuran in a dry ice bath, followed by dropwise addition of a solution of lithium bis(trimethylsilyl)amide (1 M) in toluene (530 µL, 0.53 mmol). After stirring for 30 minutes, a solution of 1-methylpiperidine-2-carbaldehyde 6b (120 mg, 0.96 mmol) in 5 mL of tetrahydrofuran was added dropwise. The reaction mixture was stirred for another 30 minutes, then warmed up to room temperature and stirred for 12 hours. The reaction mixture was concentrated under reduced pressure and the resulting residue was purified by silica gel column chromatography with elution system A to obtain the title compound (E)-N-[4-[[3-chloro-4-(2-pyridylmethoxy)phenyl]amino]-3-cyano-7-ethoxy-6-quinolyl]-3-(1-methyl-2-piperidyl)prop-2-enamide 6 (14 mg, yield 4.9%) as a yellow solid.

MS m/z (ESI): 597.3 [M+1]

$^1$H NMR (400 MHz, DMSO-d$_6$): δ 9.09 (s, 1H), 8.63 (d, 1H), 8.51 (s, 1H), 7.83-7.79 (m, 2H), 7.58-7.56 (m, 1H), 7.30-7.27 (m, 3H), 7.14-7.12 (m, 2H), 7.04 (d, 1H), 6.69-6.66 (m, 1H), 5.32 (s, 2H), 4.32-4.29 (m, 2H), 4.27-4.24 (m, 2H), 3.60-3.40 (m, 2H), 2.71 (s, 3H), 2.05-1.72 (m, 6H), 1.62 (t, 3H)

Example 7

(E)-N-[4-[(3-Chloro-4-fluoro-phenyl)amino]-7-ethoxy-quinazolin-6-yl]-3-[(2S)-1-methylpyrrolidin-2-yl]prop-2-enamide

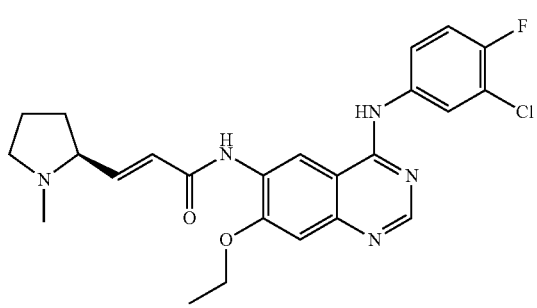

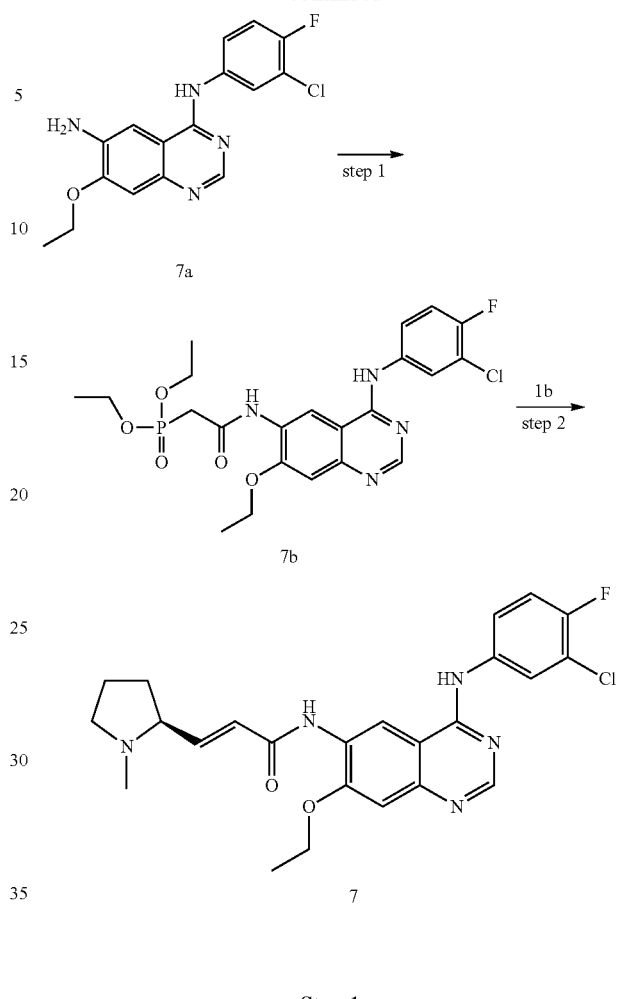

Step 1

N-[4-[(3-Chloro-4-fluoro-phenyl)amino]-7-ethoxy-quinazolin-6-yl]-2-diethoxyphosphoryl-acetamide N,N'-Carbonyldiimidazole (292 mg, 1.80 mmol) was dissolved in 4 mL of tetrahydrofuran. The mixture was heated to 50° C. in an oil bath, a solution of diethylphosphonoacetic acid (353 mg, 1.8 mmol) in 3 mL of tetrahydrofuran was added dropwise, and stirred for 1.5 hours to the next step.

N4-(3-Chloro-4-fluoro-phenyl)-7-ethoxy-quinazoline-4,6-diamine 7a (200 mg, 0.60 mmol, prepared by the well-known method: patent application WO2005028443) was dissolved in 10 mL of tetrahydrofuran, followed by dropwise addition of the above reaction solution at 50° C. After stirring for 3 hours at 40° C., the reaction mixture was concentrated under reduced pressure and extracted with dichloromethane (50 mL×3). The combined organic extracts were washed with saturated brine (50 mL×2), dried over anhydrous sodium sulfate, filtered and concentrated under reduced pressure and the resulting residue was purified by silica gel column chromatography with elution system A to obtain the title compound N-[4-[(3-chloro-4-fluoro-phenyl)amino]-7-ethoxy-quinazolin-6-yl]-2-diethoxyphosphoryl-acetamide 7b (100 mg, yield 33.3%) as a light yellow solid.

MS m/z (ESI): 511.1 [M+1]

Step 2

(E)-N-[4-[(3-Chloro-4-fluoro-phenyl)amino]-7-ethoxy-quinazolin-6-yl]-3-[(2S)-1-methylpyrrolidin-2-yl]prop-2-enamide N-[4-[(3-Chloro-4-fluoro-phenyl)amino]-7-ethoxy-quinazolin-6-yl]-2-diethoxyphosphoryl-acetamide 7b (100 mg, 0.20 mmol) was dissolved in 10 mL of tetrahydrofuran. The mixture was cooled to −78° C. in a dry ice bath, followed by dropwise addition of a solution of lithium bis(trimethylsilyl)amide (1 M) in toluene (400 μL, 0.40 mmol), and the mixture was stirred for 45 minutes, added with (2S)-1-methylpyrrolidine-2-carbaldehyde 1b (100 mg, 0.85 mmol). After stirring for another 1 hour, the reaction mixture was warmed up to room temperature and stirred for 12 hours. The reaction mixture was added with water (1 mL) and methanol (1 mL), extracted with dichloromethane (100 mL×3). The combined organic extracts were washed with saturated brine (30 mL×2), dried over anhydrous sodium sulfate, filtered and the filtrate was concentrated under reduced pressure, then the resulting residue was purified by silica gel column chromatography with elution system A to obtain the title compound (E)-N-[4-[(3-chloro-4-fluoro-phenyl)amino]-7-ethoxy-quinazolin-6-yl]-3-[(2S)-1-methylpyrrolidin-2-yl]prop-2-enamide 7 (60 mg, yield 65.2%) as a yellow solid.

MS m/z (ESI): 470.2 [M+1]

$^1$H NMR (400 MHz, DMSO-$d_6$): δ 9.78 (s, 1H), 9.53 (s, 1H), 8.91 (s, 1H), 8.52 (s, 1H), 8.13-8.15 (m, 1H), 7.79-7.81 (m, 1H), 7.39-7.43 (m, 1H), 7.26 (s, 1H), 6.67-6.69 (m, 2H), 4.26-4.31 (m, 2H), 4.09-4.10 (m, 1H), 3.17-3.15 (m, 2H), 3.08-3.04 (m, 1H), 2.77-2.79 (m, 1H), 2.87-2.82 (m, 1H), 2.23 (s, 3H), 1.74-1.76 (m, 1H), 1.47 (m, 3H)

Example 8

(E)-N-[4-[(3-Chloro-4-fluoro-phenyl)amino]-7-(2-methoxyethoxy)quinazolin-6-yl]-3-[(2R)-1-methylpyrrolidin-2-yl]prop-2-enamide

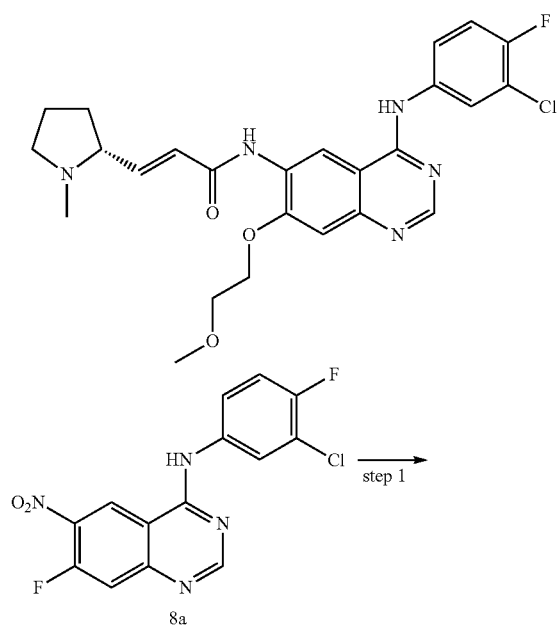

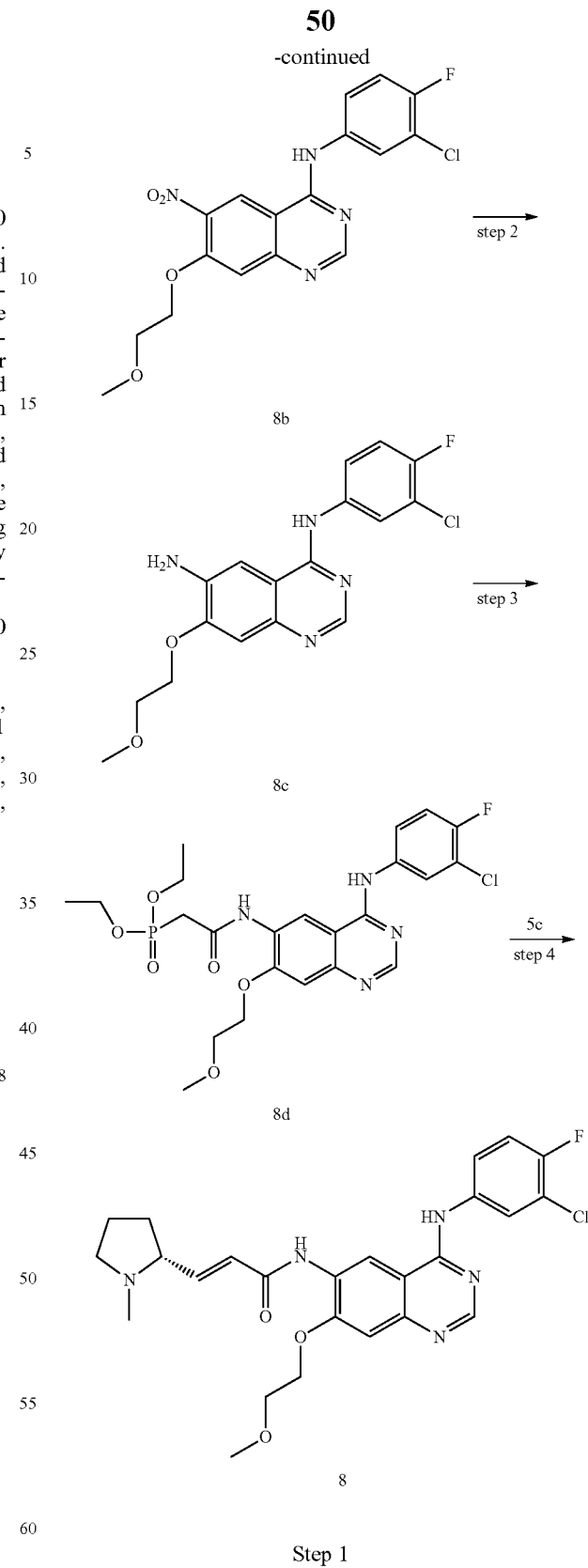

Step 1

N-(3-Chloro-4-fluoro-phenyl)-7-(2-methoxyethoxy)-6-nitro-quinazolin-4-amine 2-methoxyethanol (152 mg, 2 mmol) was dissolved in 30 mL of dimethyl sulfoxide in an ice-water bath, followed by addition of 60% sodium hydride (80 mg, 2 mmol). The mixture was warmed up to 40° C. and stirred for 2 hours, then N-(3-chloro-4-fluoro-phenyl)-7-fluoro-6-nitro-quinazolin-4-amine 8a (336 mg, 1 mmol) was added. The reaction mixture was stirred for 4 hours at 40° C., then warmed up to 50° C. and stirred for 12 hours. The reaction mixture was added with water (20 mL), filtered and the filter cake was washed with water (50 mL), dried under vacuum to obtain the title compound N-(3-chloro-4-fluoro-phenyl)-7-(2-methoxyethoxy)-6-nitro-quinazolin-4-amine 8b (392 mg, yield 100%) as a yellow solid, which was directly used in the next step.

MS m/z (ESI): 393.0 [M+1]

Step 2

N4-(3-Chloro-4-fluoro-phenyl)-7-(2-methoxyethoxy)quinazoline-4,6-diamine

N-(3-Chloro-4-fluoro-phenyl)-7-(2-methoxyethoxy)-6-nitro-quinazolin-4-amine 8b (392 mg, 1 mmol) and iron powder (392 mg, 7 mmol) were dissolved in 20 mL of acetic acid. The reaction mixture was heated to reflux for 4 hours, concentrated under reduced pressure. The residue was added with 100 mL of saturated sodium bicarbonate, extracted with dichloromethane (100 mL×3). The combined organic extracts were washed with saturated brine (50 mL×2), dried over anhydrous sodium sulfate, filtered and concentrated under reduced pressure to obtain the title compound N4-(3-chloro-4-fluoro-phenyl)-7-(2-methoxyethoxy)quinazoline-4,6-diamine 8c (200 mg, yield 55.2%) as a light yellow solid.

MS m/z (ESI): 363.1 [M+1]

Step 3

N-[4-[(3-Chloro-4-fluoro-phenyl)amino]-7-(2-methoxyethoxy)quinazolin-6-yl]-2-diethoxyphosphoryl-acetamide N,N'-Carbonyldiimidazole (292 mg, 1.80 mmol) was dissolved in 4 mL of tetrahydrofuran. The mixture was heated to 50° C. in an oil bath, a solution of diethylphosphonoacetic acid (353 mg, 1.8 mmol) in 3 mL of tetrahydrofuran was added dropwise, and stirred for 1.5 hours to the next step.

N4-(3-Chloro-4-fluoro-phenyl)-7-(2-methoxyethoxy)quinazoline-4,6-diamine 8c (200 mg, 0.55 mmol) was dissolved in 10 mL of tetrahydrofuran, followed by dropwise addition of the above reaction solution at 50° C. After stirring for 3 hours at 40° C., the reaction mixture was concentrated under reduced pressure and extracted with dichloromethane (50 mL×3). The combined organic extracts were washed with saturated brine (50 mL×2), dried over anhydrous sodium sulfate, filtered and concentrated under reduced pressure and the resulting residue was purified by silica gel column chromatography with elution system A to obtain the title compound N-[4-[(3-chloro-4-fluoro-phenyl)amino]-7-(2-methoxyethoxy)quinazolin-6-yl]-2-diethoxyphosphoryl-acetamide 8d (150 mg, yield 50.5%) as a light yellow solid.

MS m/z (ESI): 541.2 [M+1]

Step 4

(E)-N-[4-[(3-Chloro-4-fluoro-phenyl)amino]-7-(2-methoxyethoxy)quinazolin-6-yl]-3-[(2R)-1-methylpyrrolidin-2-yl]prop-2-enamide N-[4-[(3-Chloro-4-fluoro-phenyl)amino]-7-(2-methoxyethoxy)quinazolin-6-yl]-2-diethoxyphosphoryl-acetamide 8d (200 mg, 0.37 mmol) was dissolved in 10 mL of tetrahydrofuran. The mixture was cooled to −78° C. in a dry ice bath. Under argon, a solution of lithium bis(trimethylsilyl)amide (1 M) in toluene (740 μL, 0.74 mmol) was added dropwise. After stirring for 30 minutes, (2R)-1-methylpyrrolidine-2-carbaldehyde 5c (84 mg, 0.74 mmol) was added to the reaction solution. The reaction mixture was stirred for another 1 hour, then warmed up to room temperature and stirred for 12 hours. The reaction mixture was concentrated, added with 10 mL of water, extracted with dichloromethane (25 mL×3). The combined organic extracts were washed with saturated brine (30 mL×2), dried over anhydrous sodium sulfate, filtered and concentrated under reduced pressure and the resulting residue was purified by silica gel column chromatography with elution system A to obtain the title compound (E)-N-[4-[(3-chloro-4-fluoro-phenyl)amino]-7-(2-methoxyethoxy)quinazolin-6-yl]-3-[(2R)-1-methylpyrrolidin-2-yl]prop-2-enamide 8 (100 mg, yield 54.2%) as a yellow solid.

MS m/z (ESI): 500.2 [M+1]

$^1$H NMR (400 MHz, DMSO-$d_6$): δ 9.82 (s, 1H), 9.58 (s, 1H), 8.89 (s, 1H), 8.53 (s, 1H), 8.12-8.13 (m, 1H), 7.79-7.81 (m, 1H), 7.40-7.44 (m, 1H), 7.32 (s, 1H), 6.57-6.75 (m, 2H), 4.36-4.37 (m, 2H), 3.80-3.81 (m, 2H), 3.35-3.32 (m, 4H), 3.15-3.13 (m, 1H), 2.5 (s, 3H), 2.40-2.31 (m, 2H), 2.08 (m, 1H), 1.90-1.81 (m, 1H), 1.70-1.64 (m, 1H)

Example 9

(E)-N-[4-[(3-Chloro-4-fluoro-phenyl)amino]-7-ethoxy-quinazolin-6-yl]-3-[(2R)-1-methylpyrrolidin-2-yl]prop-2-enamide

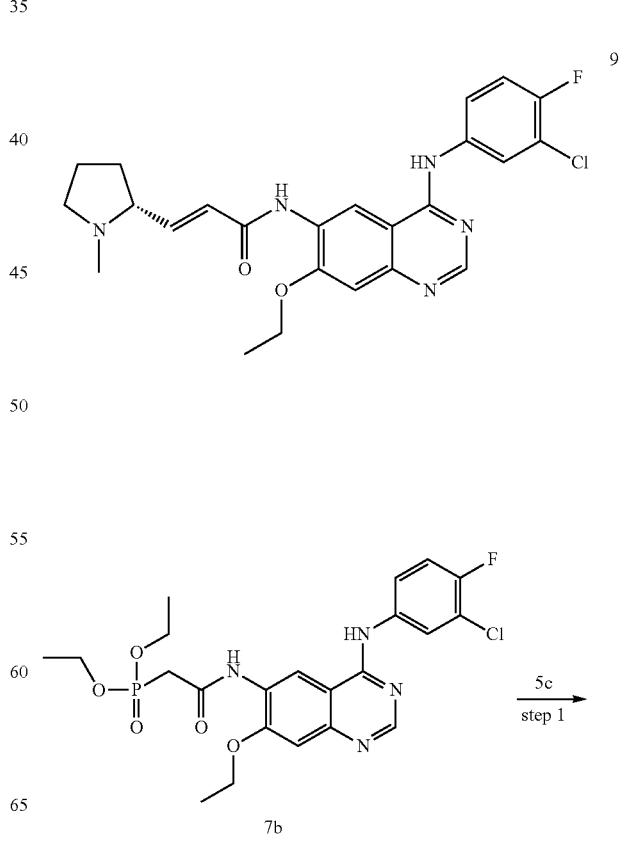

-continued

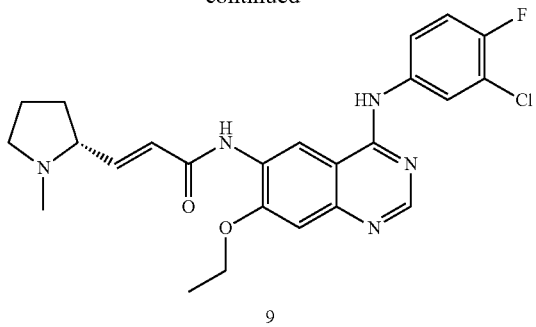

9

Step 1

(E)-N-[4-[(3-Chloro-4-fluoro-phenyl)amino]-7-ethoxy-quinazolin-6-yl]-3-[(2R)-1-methylpyrrolidin-2-yl]prop-2-enamide N-[4-[(3-Chloro-4-fluoro-phenyl)amino]-7-ethoxy-quinazolin-6-yl]-2-diethoxyphosphoryl-acetamide 7b (300 mg, 0.59 mmol) was dissolved in 10 mL of tetrahydrofuran. The mixture was cooled to −78° C. in a dry ice bath. Under argon, a solution of lithium bis(trimethylsilyl)amide (1 M) in toluene (1.2 mL, 1.18 mmol) was added dropwise. After the mixture was stirred for 30 minutes, (2R)-1-methylpyrrolidine-2-carbaldehyde 5c (133 mg, 1.18 mmol) was added, and the mixture was stirred for another 1 hour, then warm up to room temperature and stirred for 12 hours. The reaction mixture was concentrated, added with 10 mL of water, extracted with dichloromethane (25 mL×3). The combined organic extracts were washed with saturated brine (30 mL×2), dried over anhydrous sodium sulfate, filtered and concentrated under reduced pressure and the resulting residue was purified by silica gel column chromatography with elution system A to obtain the title compound (E)-N-[4-[(3-chloro-4-fluoro-phenyl)amino]-7-ethoxy-quinazolin-6-yl]-3-[(2R)-1-methylpyrrodin-2-yl]prop-2-enamide 9 (130 mg, yield 47.3%) as a yellow solid.

MS m/z (ESI): 470.2 [M+1]

$^1$H NMR (400 MHz, DMSO-d$_6$): δ 9.79 (s, 1H), 9.53 (s, 1H), 8.93 (s, 1H), 8.53 (s, 1H), 8.12-8.15 (m, 1H), 7.79-7.83 (m, 1H), 7.40-7.45 (m, 1H), 7.27 (s, 1H), 6.67-6.73 (m, 1H), 6.56-6.60 (m, 1H), 4.27-4.32 (m, 2H), 4.09-4.10 (m, 1H), 3.17 (m, 2H), 3.04 (m, 1H), 2.77-2.79 (m, 1H), 2.18-2.16 (m, 1H), 2.21 (s, 3H), 1.74-1.76 (m, 1H), 1.47 (t, 3H)

Example 10

(E)-N-[4-[[3-Chloro-4-(2-pyridylmethoxy)phenyl]amino]-3-cyano-7-ethoxy-6-quinolyl]-3-(1-methylpyrrolidin-2-yl)prop-2-enamide

10

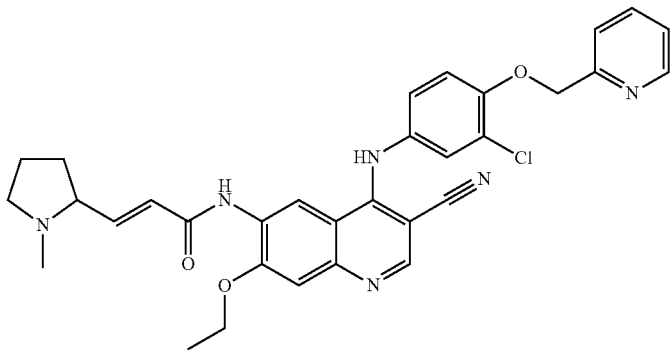

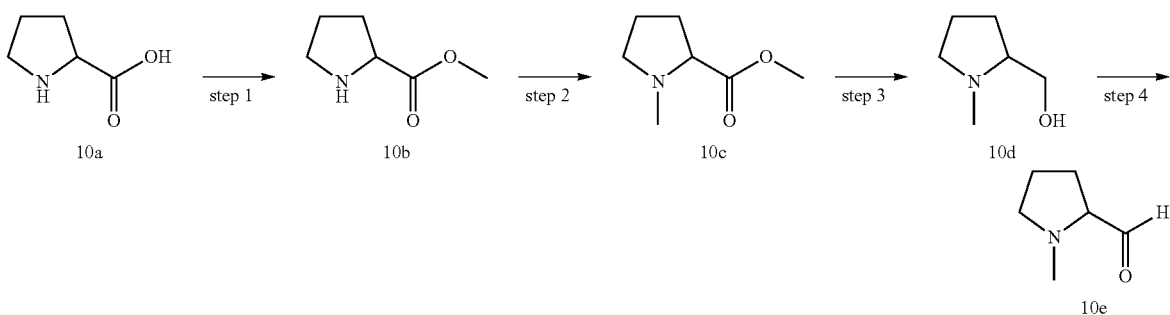

-continued

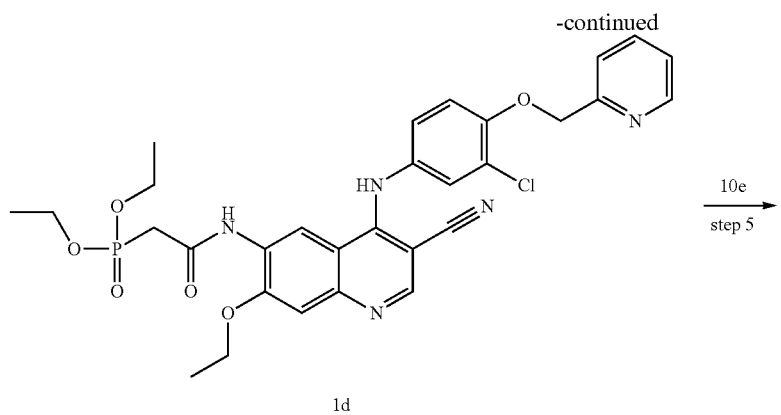

Step 1

Methyl pyrrolidine-2-carboxylate 7 mL of thionyl chloride was dissolved in 50 mL of methanol in an ice-water bath, followed by addition of pyrrolidine-2-carboxylic acid 10a (5 g, 43.40 mmol). The mixture was warmed up to room temperature and stirred for 24 hours. The mixture was concentrated under reduced pressure to obtain methylpyrrolidine-2-carboxylate 10b (10 g) crude product as a white solid, which was directly used in the next step without purification.

MS m/z (ESI): 130.1 [M+1]

Step 2

Methyl 1-methylpyrrolidine-2-carboxylate

Methyl pyrrolidine-2-carboxylate 10b crude product (5 g) was dissolved in 100 mL of methanol. The solution was cooled to 0~5° C. in an ice-water bath, followed by addition of 13 mL of 40% formaldehyde. The reaction mixture was warmed up to room temperature and stirred for 2 hours, then cooled to 0~5° C. in an ice-water bath, and sodium cyanoborohydride (5.45 g, 87.20 mmol) was added in batches. The reaction mixture was warmed up to room temperature and stirred for 24 hours. The mixture was concentrated under reduced pressure and added with 5 mL of water, extracted with dichloromethane (5 mL×3). The combined organic extracts were dried over anhydrous sodium sulfate, filtered and concentrated under reduced pressure to obtain methyl 1-methylpyrrolidine-2-carboxylate 10c (4.7 g, yield 70.1) crude product as a brown oil.

MS m/z (ESI): 144.1 [M+1]

Step 3

(1-Methylpyrrolidin-2-yl)methanol

Diisobutyl aluminium hydride (60 mL, 66 mmol) was added dropwise to a solution of methyl 1-methylpyrrolidine-2-carboxylate 10c (4.7 g, 33 mmol) in 50 mL of dichloromethane. The reaction mixture was stirred for 6 hours in an ice-water bath, followed by addition of 10 mL of methanol. The reaction mixture was concentrated under reduced pressure to obtain the title compound (1-methylpyrrolidin-2-yl)methanol 10d (1.8 g, yield 47.4%) as a brown oil.

Step 4

1-Methylpyrrolidine-2-carbaldehyde

Dimethyl sulfoxide (2.2 mL, 31.20 mmol) was dissolved in 20 mL of dichloromethane in a dry ice-acetone bath, followed by addition of oxalyl chloride (2 mL, 23.40 mmol). After stirring for 45 minutes at −18° C., (1-methylpyrrolidin-2-yl)methanol 10d (1.8 g, 15.60 mmol) was added. After stirring for another 45 minutes, triethylamine (6.5 mL, 46.80 mmol) was added. The reaction mixture was warmed up to room temperature and stirred for 1 hour. The reaction mixture was washed with saturated brine (50 mL), dried over anhydrous sodium sulfate, filtered and concentrated under reduced pressure and the resulting residue was purified by alkaline alumina column chromatography with elution system A to obtain 1-methylpyrrolidine-2-carbaldehyde 10e (1 g, yield 56.8%) as a brown oil.

Step 5

(E)-N-[4-[[3-Chloro-4-(2-pyridylmethoxy)phenyl]amino]-3-cyano-7-ethoxy-6-quinolyl]-3-(1-methylpyrrolidin-2-yl)prop-2-enamide N-[4-[[3-Chloro-4-(2-pyridylmethoxy)phenyl]amino]-3-cyano-7-ethoxy-6-quinolyl]-2-diethoxyphosphoryl-acetamide 1d (3 g, 4.40 mmol) was dissolved in 30 mL of tetrahydrofuran in a dry ice bath, followed by dropwise addition of a solution of lithium bis(trimethylsilyl)amide (1 M) in toluene (9.6 mL, 8.80 mmol). After the mixture was stirred for 30 minutes, a solution of 1-methylpyrrolidine-2-carbaldehyde 10e (1 g, 8.80 mmol) in 5 mL of tetrahydrofuran was added dropwise. The reaction mixture was stirred for another 30 minutes, then warmed up to room temperature and stirred for 24 hours. The reaction mixture was concentrated under reduced pressure and the resulting residue was purified by silica gel column chromatography with elution system A to obtain the title compound (E)-N-[4-[[3-chloro-4-(2-pyridylmethoxy)phenyl]amino]-3-cyano-7-ethoxy-6-quinolyl]-3-(1-methylpyrrolidin-2-yl)prop-2-enamide 10 (500 mg, yield 20.8%) as a yellow solid.

MS m/z (ESI): 583.2 [M+1]

$^1$H NMR (400 MHz, DMSO-$d_6$): δ 11.59 (s, 1H), 11.28 (s, 1H), 9.19 (s, 1H), 9.05 (s, 1H), 8.71 (d, 1H), 8.09-8.07 (m, 1H), 7.74-7.68 (m, 3H), 7.56-7.55 (m, 1H), 7.45-7.37 (m, 2H), 7.04-7.00 (m, 1H), 6.88-6.84 (m, 1H), 5.43 (s, 2H), 4.38 (dd, 2H), 4.10 (m, 2H), 3.63-3.60 (m, 1H), 3.13-3.08 (m, 1H), 2.73-2.72 (m, 3H), 2.31-2.29 (m, 1H), 2.08-2.02 (m, 2H), 1.53 (t, 3H)

Test Examples

Biological Assays

Example 1

EGFR Cell Proliferation Inhibition Assay

The following in vitro assay is to determine the activity of the compounds of the invention for inhibiting the proliferation of human epidermoid carcinoma A431 cells, which has high expression of EGFR.

The following in vitro assay is to determine the activity of the tested compounds for inhibiting the proliferation of cancer cells, which has high expression of EGFR. The activity is represented by the $IC_{50}$ value. The general procedures of the assay are given as follows: The cancer cells A431 that highly expressing EGFR (Institute of biochemistry and cell biology) were chosen and seeded to 96-well cell culture plate at a suitable concentration (e.g., 5000 cells/mL medium). The cells then were incubated in carbon dioxide ($CO_2$) incubator until they reached 85% confluency. Then, the cell culture medium was replaced by fresh one with tested compounds added in it at serial concentrations (general 6 to 7 concentrations). Then the cells were put back to the incubator and cultured continuously. 72 hours later, the activity of the tested compounds for inhibiting the cell proliferation was determined by using Sulforhodamine B (SRB) method. $IC_{50}$ value on tested cells are calculated by the data of inhibition rates of serial concentrations of the tested compounds.

The Activity of the Compounds of the Invention:

The biological activity of the compounds of the invention was tested by using the assay described above. The $IC_{50}$ values were measured and showed in table below:

| Example No. | $IC_{50}$ (EGFR/A431)(μM) |
|---|---|
| 1 | 0.022 |
| 2 | 0.003 |
| 3 | 0.036 |
| 5 | 0.045 |
| 9 | 0.008 |

Conclusion: the compounds of the present invention had obvious activity for inhibiting the proliferation of A431 cell.

Example 2

EGFR Kinase Activity Assay

The in vitro EGFR kinase activity was tested by the following assay.

The following assay may be used to determine the activity of the compounds of the invention for inhibiting EGFR kinase activity. The half maximal inhibitory concentration $IC_{50}$ (the concentration of the tested compound showing 50% inhibition of the enzyme activity) of each compound was determined by incubating several different concentrations of the tested compounds with a specific enzyme and substrate. EGFR kinase used in this assay is a human-derived recombinant protein (Cell signaling technology, #7908), which was reacted with peptide substrate and different concentrations of tested compounds in a buffer solution containing 60 mM HEPES (pH7.5), 5 mM $MgCl_2$, 5 mM $MnCl_2$, 3 μM $Na_3VO_4$, 1.25 M DTT (1000×) and 20 μM ATP at 25° C., for 45 minutes. The EGFR kinase activity was determined by using a Time-Resolved fluorescence method.

The Activity of the Compounds of the Invention:

The biological activity of the compounds of the invention was tested by using the assay described above. The $IC_{50}$ values were measured and showed in table below:

| Example No. | $IC_{50}$ (EGFR/BIO) (μM) |
|---|---|
| 1 | 0.048 |
| 2 | 0.006 |
| 3 | 0.059 |
| 5 | 0.013 |
| 7 | 0.004 |
| 8 | 0.002 |
| 9 | 0.002 |

Conclusion: the compounds of the present invention had obvious activity for inhibiting the proliferation of EGFR Kinase.

Pharmacokinetics Assay

Test Example 1

The Pharmacokinetics Assay of the Compounds of Example 1 and Example 5 of the Present Invention 1. Abstract The compounds of Example 1 and Example 5 of the present invention were administrated intragastrically to rats to determine the drug concentration in plasma at different time points by LC/MS/MS method. The pharmacokinetic behavior of the compounds of the present invention was studied and evaluated in rats.

2. Protocol
2.1 Samples
Compounds of Example 1 and Example 5
2.2 Experimental Animals
8 healthy adult SD rats, male and female in half, were purchased from SINO-BRITSH SIPPR/BK LAB. ANIMAL LTD., CO, License number: SCXK (Shanghai) 2003-0002
2.3 Preparation of the Tested Compounds
The right amount of compounds were weighted and grinded with 0.5% Sodium Carboxymethyl cellulose uniformly, suspended them with 1% tween 80 to 2.5 mg/mL of suspension before use.
2.4 Administration
8 Healthy adult adult SD rats, male and female in half, after an overnight fast, were administered intragastrically at a dose of 25.0 mg/kg, at a volume of 10 mL/kg.
2.5 Sample Collection
8 Healthy adult adult SD rats, male and female in half, were divided into 2 groups. After an overnight fast, the rats were administered intragastrically at a dose of 25.0 mg/kg. Blood samples (0.2 mL) were taken from orbital sinus at pre administration and at 0.5, 1.0, 2.0, 3.0, 4.0, 5.0, 7.0, 9.0, 12.0, 24.0 and 30.0 hours post administration, which were stored in heparinized tubes and centrifuged for 10 minutes at 3,500 rpm. The plasma samples were stored at $-20°$ C. until analysis. The rats were fed 2 hours after administration.
3. Operation
50 μL of rat plasmas taken at various time points after administration were mixed with 50 μL of standard series solution to obtain plasma concentration of 50.0, 100, 200, 500, 1000, 2000, 5000 ng/mL. 150 μL methanol was added and then the mixture was mixed for 3 minute using a vortexer and centrifuged for 10 minutes at 13,500 rpm. 10 μL of the supernatant was analyzed by LC-MS/MS. The main pharmacokinetic parameters were caculated by DAS 2.0 software.
4. Results of Pharmacokinetic Parameters
Pharmacokinetic Parameters of the compounds of the present invention were shown as follows:

| Number | Plasma Conc. Cmax (μg/mL) | Area Under Curve AUC (ng/mL*h) | Half-Life $t_{1/2}$ (h) | Mean Residence Time MRT (h) | Clearance CL/F (l/h/kg) | Apparent Distribution Volume Vz/F (l/kg) |
|---|---|---|---|---|---|---|
| Example 1 | 4.48 ± 1.88 | 52.58 ± 38.96 | 4.04 ± 1.39 | 7.78 ± 1.89 | 0.76 ± 0.53 | 3.71 ± 1.68 |
| Example 5 | 6.47 ± 1.81 | 52.81 ± 23.59 | 3.4 ± 0.45 | 7.66 ± 0.75 | 0.53 ± 0.18 | 2.6 ± 0.94 |

Conclusion: the compounds of the present invention had good absorption in pharmacokinetics and the pharmacokinetic characteristics improved obviously.

The Therapeutic Effects Against Xenografts of Calu-3 Human Lung Cancer in Nude Mice 1. Abstract
The therapeutic effect of the compound of Example 1 against xenografts of Calu-3 human lung cancer in nude mice was estimated. The compound of Example 1 markedly inhibited the growth of Calu-3 human lung cancer, and the tested mice were well tolerant.
2. Purpose
The therapeutic effects of the compounds of Example 1 and Example 5 against xenografts of Calu-3 human lung cancer in nude mice was estimated and compared.
3. Tested Drugs
Drugs Name and batch of drugs: the compounds of Example 1 and Example 5

Preparation method: The compounds of Example 1 and Example 5 were prepared to corresponding concentration by using distilled water containing 0.1% Tween-80.
4. Experimental Animals
BALB/cA-nude mice, 6 to 7 weeks old, ♀, purchased from Slaccas Experimental Animal LTD., CO.
Certificate No.: SCXK 2007-0005. Environment: SPF level.
5. Experimental Protocol
Nude mice were hypodermic inoculated Calu-3 human lung cancer cell. After tumors grew to 150-250 mm³, mice were randomly divided into teams (d0).
The volume of tumors and the weigh of the mice were measured and recorded for 2-3 times per week.
The calculation formula of the volume of tumor (V) is: $V=\frac{1}{2} \times a \times b^2$, a: length of tumor, b: width of tumor.
6. Result
The compound of Example 1 markedly inhibited the growth of Calu-3 human lung cancer. Low dose (100 mg/kg) of the compound of Example 1 reduced 2/6 of the tumor volume, high dose (200 mg/kg) of the compound of Example 1 reduced 1/6 of the tumor volume and completely degrade other 1/6 of the tumor. Low dose (100 mg/kg) of the compound of Example 5 reduced 3/6 of the tumor volume, high dose (200 mg/kg) of the compound of Example 5 reduced 4/6 of the tumor volume. Moreover, the mice were well tolerant to the compounds of Example 1 and Example 5 according to the present administration protocol.

What is claimed is:

1. A compound of formula (I), or a tautomer, racemate, enantiomer, diastereoisomer or mixture thereof, or a pharmaceutically acceptable salt thereof:

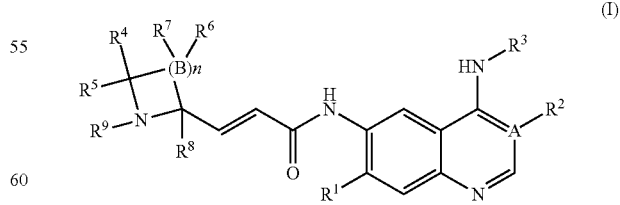

wherein:

A is carbon atom, $R^1$ is selected from the group consisting of hydrogen and alkoxyl; wherein said alkoxyl is optionally substituted with one or more groups selected from the group consisting of halogen and alkoxyl;
$R^2$ is cyano;
$R^3$ is a radical having the following formula:

wherein:
- D is selected from the group consisting of aryl and heteroaryl, wherein said aryl or heteroaryl is each independently optionally substituted with one or more groups selected from the group consisting of halogen, alkyl and trifluoromethyl;
- T is selected from the group consisting of —(CH$_2$)r-, —O(CH$_2$)r-, —NH(CH$_2$)r- and —S(O)r(CH$_2$)r-; and
- L is selected from the group consisting of aryl and heteroaryl, wherein said aryl or heteroaryl is each independently optionally substituted with one or more groups selected from the group consisting of halogen and alkyl;
- $R^4$ and $R^5$ are each independently selected from the group consisting of hydrogen, alkyl, alkoxyl, hydroxyl, hydroxyalkyl, halogen, carbonyl, amino, cyano, nitro, carboxyl and carboxylic ester;
- B is selected from the group consisting of carbon atom, oxygen atom and S(O)r;
- when B is carbon atom, $R^6$ and $R^7$ are each independently selected from the group consisting of hydrogen, alkyl, alkoxyl, hydroxyl, hydroxyalkyl, halogen, carbonyl, amino, cyano, nitro, carboxyl and carboxylic ester;
- when B is oxygen atom or S(O)r, $R^6$ and $R^7$ are absent;
- $R^8$ is selected from the group consisting of hydrogen and alkyl;
- $R^9$ is selected from the group consisting of hydrogen, alkyl, aryl, carboxyl and carboxylic ester;
- r is 0, 1, or 2; and
- n is 1, 2, 3, 4, or 5.

2. The compound according to claim 1, the tautomer, racemate, enantiomer, diastereoisomer or mixture thereof, or the pharmaceutically acceptable salt thereof, wherein $R^1$ is alkoxyl.

3. The compound according to claim 1, the tautomer, racemate, enantiomer, diastereoisomer or mixture thereof, or the pharmaceutically acceptable salt thereof, wherein n is 2.

4. The compound according to claim 1, the tautomer, racemate, enantiomer, diastereoisomer or mixture thereof, or the pharmaceutically acceptable salt thereof, comprising a compound having the following formula (II) or a tautomer, racemate, enantiomer, diastereomer or mixture thereof, or a pharmaceutically acceptable salt thereof:

(II)

wherein A, $R^1$ to $R^5$, $R^8$, $R^9$ and n are as defined in claim 1.

5. The compound according to claim 4, the tautomer, racemate, enantiomer, diastereoisomer or mixture thereof, or the pharmaceutically acceptable salt thereof, wherein $R^1$ is alkoxyl.

6. The compound according to claim 4, the tautomer, racemate, enantiomer, diastereoisomer or mixture thereof, or the pharmaceutically acceptable salt thereof, wherein n is 2.

7. The compound according to claim 1, the tautomer, racemate, enantiomer, diastereoisomer or mixture thereof, or the pharmaceutically acceptable salt thereof, wherein the compound is selected from the group consisting of:

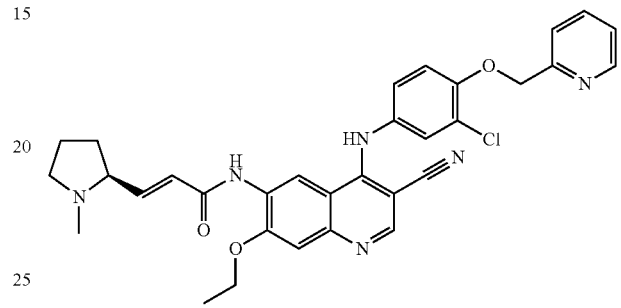

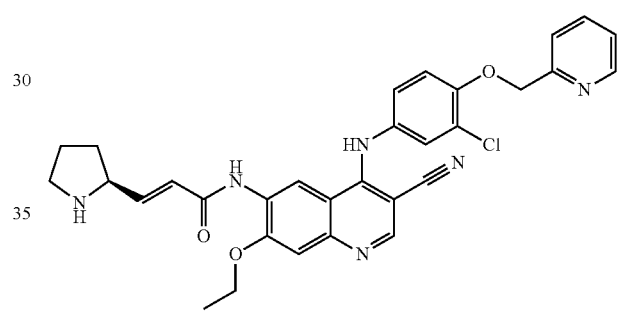

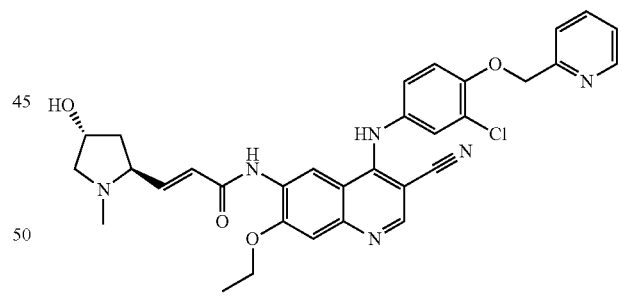

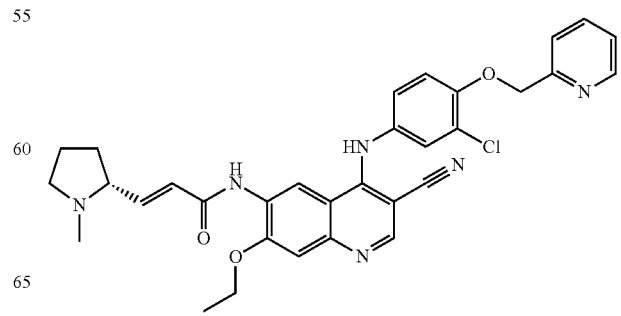

-continued

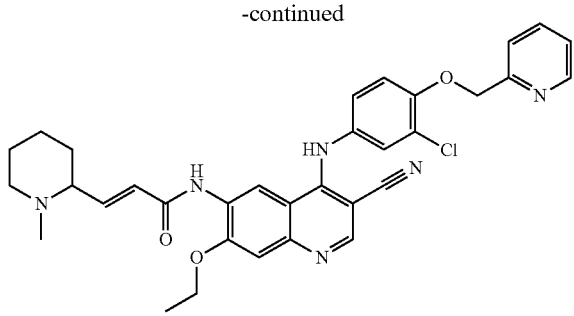

and

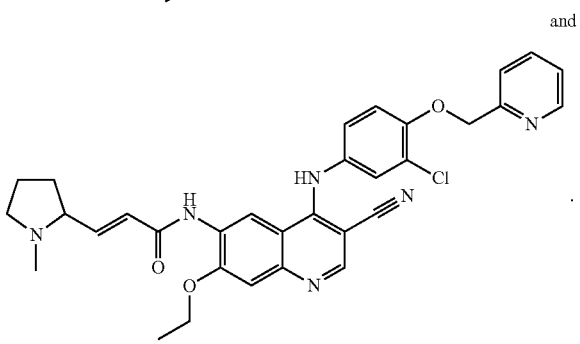

8. A compound of formula (IA),

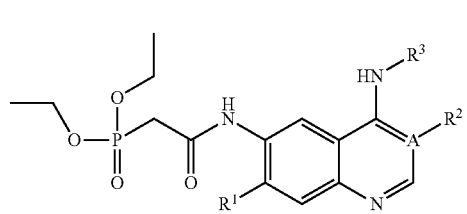

wherein:
A is carbon atom,
R¹ is selected from the group consisting of hydrogen and alkoxyl; wherein said alkoxyl is further substituted with one or more groups selected from the group consisting of halogen and alkoxyl;
R² is cyano; and
R₃ is a radical having the following formula:

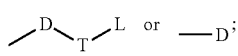

wherein:
D is selected from the group consisting of aryl and heteroaryl, wherein said aryl or heteroaryl is each independently optionally substituted with one or more groups selected from the group consisting of halogen, alkyl and trifluoromethyl;
T is selected from the group consisting of —(CH₂)r-, —O(CH₂)r-, —NH(CH₂)r- and —S(O)r(CH₂)r-;
L is selected from the group consisting of aryl and heteroaryl, wherein said aryl or heteroaryl is each independently optionally substituted with one or more groups selected from the group consisting of halogen and alkyl; and
r is 0, 1, or 2.

9. A process of preparing the compound of formula (IA) according to claim 8, comprising:

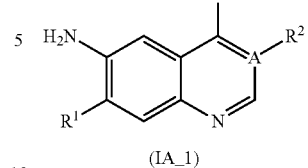

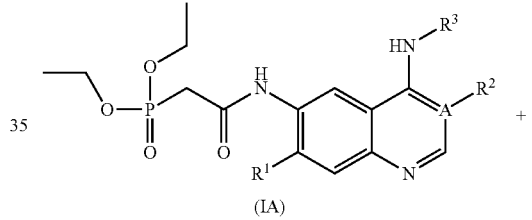

reacting the compound of formula (IA_1) with diethylphosphonoacetic acid in the presence of a condensation agent to obtain the compound of formula (IA); wherein A, R¹, R² and R³ are defined as those in claim 8.

10. A process of preparing the compound of formula (I) according to claim 1, comprising:

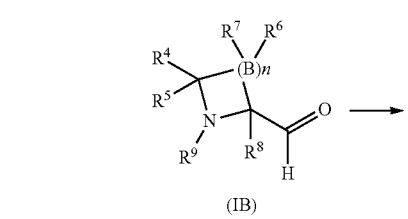

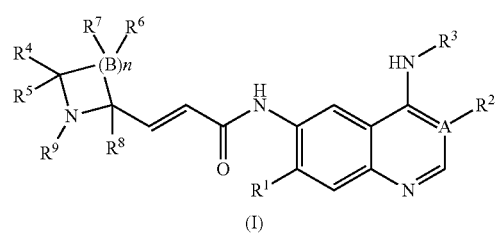

reacting the compound of formula (IA) with lithium bis(trimethylsilyl)amide to obtain a reaction solution, reacting the reaction solution with the compound of formula (IB) to obtain the compound of formula (I); wherein A, B, n, and R¹ to R⁹ are defined as those in claim 1.

11. A process of preparing the compound of formula (II) according to claim 4, comprising:

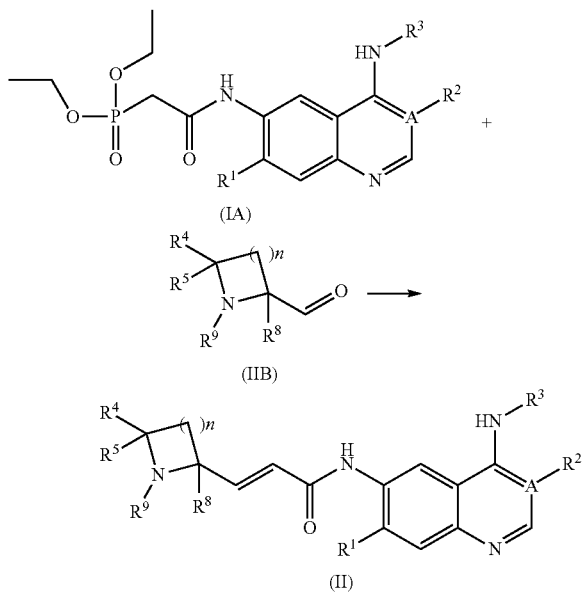

reacting the compound of formula (IA) with lithium bis(trimethylsilyl)amide to obtain a reaction solution, reacting the reaction solution with the compound of formula (IIB) to obtain the compound of formula (II); wherein A, n, $R^1$ to $R^5$, $R^8$ and $R^9$ are defined as those in claim 4.

12. A pharmaceutical composition comprising a therapeutically effective amount of the compound according to claim 1, the tautomer, racemate, enantiomer, diastereomer or mixture thereof, or the pharmaceutically acceptable salt thereof, and a pharmaceutically acceptable carrier.

13. A process of preparing a pharmaceutical composition, comprising combining the compound of formula (I) according to claim 1, the tautomer, racemate, enantiomer, diastereomer or mixture thereof, or the pharmaceutically acceptable salt thereof with a pharmaceutically acceptable carrier or a diluent agent.

14. A method of regulating the catalytic activity of a protein kinase, comprising contacting the protein kinase with a compound of formula (I) according to claim 1, the tautomer, racemate, enantiomer, diastereomer or mixture thereof, or the pharmaceutically acceptable salt thereof; wherein the protein kinase is selected from the group consisting of EGFR receptor tyrosine kinases and HER-2 receptor tyrosine kinases.

15. A method of treating a breast cancer in a subject in need thereof, comprising administrating to the subject a therapeutically effective amount of the compound of formula (I) according to claim 1, the tautomer, racemate, enantiomer, diastereomer or mixture thereof, or the pharmaceutically acceptable salt thereof.

16. A method of regulating the catalytic activity of a protein kinase, comprising contacting the protein kinase with the pharmaceutical composition according to claim 12, wherein the protein kinase is selected from the group consisting of EGFR receptor tyrosine kinases and HER-2 receptor tyrosine kinases.

17. A method of treating a breast cancer in a subject in need thereof, comprising administrating to the subject a therapeutically effective amount of the pharmaceutical composition according to claim 12.

* * * * *